(12) United States Patent
Veselkina et al.

(10) Patent No.: US 9,249,115 B2
(45) Date of Patent: Feb. 2, 2016

(54) N,N¹ SUBSTITUTED PIPERAZINES HAVING COMBINED ANTIAGGREGANT, ANTICOAGULANT AND VASODILATORY ACTIVITY, AND METHOD FOR PRODUCING SAME

(75) Inventors: Olga Sergejevna Veselkina, St. Petersburg (RU); Nikolay Borisovich Viktorov, St. Petersburg (RU); Nikolay Nikolaevich Petrishchev, St. Petersburg (RU); Yuliya Vyacheslavovna Poplavskaya, St. Petersburg (RU)

(73) Assignee: Vertex Closed Joint Stock Company, St. Petersburg (RU)

( * ) Notice: Subject to any disclaimer, the term of this patent is extended or adjusted under 35 U.S.C. 154(b) by 38 days.

(21) Appl. No.: 13/976,544

(22) PCT Filed: Nov. 8, 2011

(86) PCT No.: PCT/RU2011/000866
§ 371 (c)(1),
(2), (4) Date: Jun. 27, 2013

(87) PCT Pub. No.: WO2012/091625
PCT Pub. Date: Jul. 5, 2012

(65) Prior Publication Data
US 2013/0267707 A1 Oct. 10, 2013

(51) Int. Cl.
C07D 295/195 (2006.01)
C07D 295/096 (2006.01)
A61K 31/495 (2006.01)
C07D 295/08 (2006.01)
C07D 295/14 (2006.01)
C07D 295/18 (2006.01)
C07D 295/22 (2006.01)
C07D 295/26 (2006.01)

(52) U.S. Cl.
CPC .......... *C07D 295/096* (2013.01); *A61K 31/495* (2013.01); *C07D 295/08* (2013.01); *C07D 295/14* (2013.01); *C07D 295/18* (2013.01); *C07D 295/195* (2013.01); *C07D 295/22* (2013.01); *C07D 295/26* (2013.01)

(58) Field of Classification Search
CPC .................................................. C07D 295/195
See application file for complete search history.

(56) References Cited

FOREIGN PATENT DOCUMENTS

WO  WO 9810763 A1 * 3/1998

OTHER PUBLICATIONS

American Chemical Society (ACS). STN Chemical Abstract Service (CAS) RN Database. © 2013.*
Southwick, P.L., et al. "The Synthesis of 1-Amidino-4-Aroylpiperazines." Organic Preparations & Procedures Int. (1976), vol. 8, No. 5, pp. 205-210.*
University of Iowa. "Acids and Bases." (c) Jan. 2009. Available from: <http://web.archive.org/web/20090501000000*/http://www.uiowa.edu/~c004121/notes/ch02_3.pdf >.*
"Alkane." (c) Apr. 24, 2009. Available from: <http://web.archive.org/web/20090424073225/http://en.wikipedia.org/wiki/Alkane>.*
U.S. Metric Association. "Metric system temperature (kelvin and degrees Celsius)." (c) Aug. 2009. Available from: <http://web.archive.org/web/20090831102052/http://lamar.colostate.edu/~hillger/temps.htm >.*
Protiva, M., et al. "1-(2,4,6-Trimethylbenzyl)Piperazine and Some of Its 4-Substituted Derivatives: Synthesis and Pharmacological Screening." Collection Czechoslov. Chem. Commun. (1976), vol. 41, pp. 1035-1041.*
U.S. National Library of Medicine. "4-Benzylpiperazine-1-carboxamidine hemisulfate." Create Date: Jul. 19, 2005. Available from: <http://pubchem.ncbi.nlm.nih.gov/compounds/2756652#section=Canonical-SMILES >.*
Patani, G.A., et al. "Bioisosterism: A Rational Approach in Drug Design." Chem. Rev. (1996), vol. 96, pp. 3147-3176.*

* cited by examiner

*Primary Examiner* — Andrew D Kosar
*Assistant Examiner* — John S Kenyon
(74) *Attorney, Agent, or Firm* — Aleksandr Smushkovich

(57) ABSTRACT

The invention relates to derivatives of N,N'-substituted piperazines of the general formula (I):

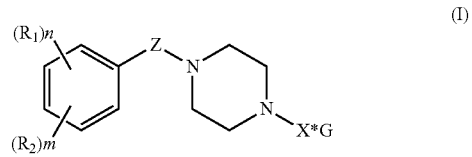

where $R^1$ and $R^2$ denote linear or branched $(C_1-C_4)$alkyl, linear or branched $(C_1-C_4)$alkoxy, $CH_3C(=O)O$ or halogen; n=1-5; m=0-3; Z denotes $CH_2$, $C=O$ or $SO_2$; X denotes $C(=NH)NH_2$, $C(=NH)NHC(=NH)NH_2$ or $CH_2(CHR^3)$ $pCH_2SO_3H$, where $R^3$ denotes H, OH, $CH_3C(=O)O$ or $HOSO_2O$ and p=0-1; and G denotes low-molecular-weight organic or mineral acid, sodium, potassium or ammonium cations, or water. Said derivatives have antiaggregant, anticoagulant and vasodilatory properties. The invention further relates to a method for producing said derivatives by reacting N-substituted piperazines either with carboxamide amidating agents or salts thereof, or with haloalkyl sulfonic acids or salts thereof in organic solvents or in water in the presence of bases. The compounds may be used for the prophylaxis and treatment of disorders of the hemostatic system.

17 Claims, No Drawings

N,N¹ SUBSTITUTED PIPERAZINES HAVING COMBINED ANTIAGGREGANT, ANTICOAGULANT AND VASODILATORY ACTIVITY, AND METHOD FOR PRODUCING SAME

CROSS-REFERENCES TO RELATED APPLICATIONS

This application is a U.S. national stage application of a PCT application PCT/RU2011/000866 filed on 8 Nov. 2011, whose disclosure is incorporated herein in its entirety by reference, which PCT application claims priority of a Russian Federation application RU2010154824 filed on 30 Dec. 2010.

FIELD OF THE INVENTION

The present invention relates to the field of pharmaceutical chemistry namely novel organic compounds influencing on haemostasis system showing antiaggregant, anticoagulant and vasodilator properties and synthesis thereof.
Particularly the invention relates to N,N'-substituted piperazines, possessing combined antiaggregant, anticoagulant and vasodilatory action on the body with general formula (I):

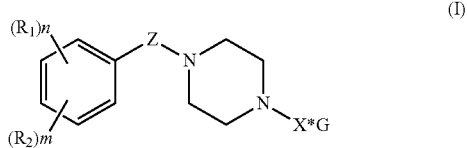

where $R^1$, $R^2$: linear or branched alkyl ($C_2 \div C_4$), linear or branched alkoxy($C_1 \div C_4$), $CH_3C(=O)O$, halogen; $n=1 \div 5$; $m=0 \div 3$; $Z=CH_2$, $C=O$, $SO_2$; X: $C(=NH)NH_2$, $C(=NH)NHC(=NH)NH_2$, $CH_2(CHR^3)pCH_2SO_3H$, where $R^3$=H, OH, $CH_3C(=O)O$, $OSO_3H$; $p=0 \div 1$; G is one of the following: low molecular weight ($C_2 \div C_4$) organic acid, or mineral acid, or sodium, or potassium, or ammonium cations, or water.

BACKGROUND OF INVENTION

Haemostasis system diseases, in particular thrombosis, vasoconstriction, play the key role in pathogenesis of coronary and cerebral blood circulation disturbances, that makes the treatment of mentioned diseases to be quite essential. The progress in therapy and prophylaxis of haemostasis disturbances is associated to a large extent with application of medical agents based on physiologically active compounds of different chemical nature and pharmacological action.

The prescription of antithrombotic drugs reduces the total risk of development of cardiovascular accidents by one quarter, nonfatal myocardial infarction by one third, nonfatal stroke by one quarter, vascular death by one sixth [McConnel H.//Br. Med. J. 2002. V. 324. P. 71-86]. In this case the basic ways of antithrombotic therapy are thrombocyte aggregation inhibition, aimed action on hemocoagulation system, reduction of endothelium thrombocyte activity. Despite the large amount of drugs capable to suppress thrombocyte activity and aggregation ability, their clinical efficiency against cardiovascular system diseases, that require antiaggregant treatment, is proven only in the case of three groups of agents—acetylsalicylic acid (ASA), thienopyridines (ticlopidine, clopidogrel, prasugrel), and thrombocyte glycoprotein receptor blockers.

Aspirin (acetylsalicylic acid—ASA) is considered as practically the only one drug that is applied for the purpose of primary cardiovascular disease prophylaxis [ANN Intern. Med. 2002. V. 136. P. 161-172], the efficiency and safety of which has been proved by the results of numerous investigations [Circulation. 2004. V. 110. P. 2361-2367; 30th International Stroke Conference. 2005, Abstr. P87].

The disadvantages of ASA should be attributed to prostacyclin synthesis suppression, bleeding risk, ASA-induced gastropathy that worsen tolerance and reduces the medication adherence by the patients, patient drug resistance [J. Thromb. Haemost. 2003. N1. P. 1710-1713; BMJ 2004. V. 328. P. 477-479; Brit. J. Clin. Pharmacol. 2008. V. 66. N2. P. 222-232].

The application of phosphodiesterase inhibitor—dipyridamole is known to reduce the frequency of ischemic transient attack development and strokes, lethality after cerebrovascular pathology. Dipyridamole has similar therapeutic effect to ASA; their combined application leads to the improvement of treatment efficiency [Future Medicine. 2005. V. 1. N1. P. 19-26]. However, dipyridamole application can provoke undesirable side effects. Thus, in the case of obstructing artery atherosclerosis and the presence of considerable amount of collaterals the drug can cause the development of steal syndrome. Therefore dipyridamole prescription is contraindicated in the case of critical coronary syndrome and myocardial infarction [Int. Med. J. 2008. V. 1. N1. P. 8-14].

Thienopyridine group representatives among antiaggregant agents are ticlopidine, clopidogrel, and prasugrel. These substances are prodrugs, it means that their therapeutic effect is achieved due to pharmacological activity of their active metabolites. The advantages of ticlopidine are reduction of stroke probability by 20%, reduction of its unfavorable outcomes and cerebral ischemia or vascular death by 10% [Ann. Intern. Med. 1998. V. 129. N5. P. 394-405]. The disadvantages of the drug are its low tolerance and frequently appearing dermal (4-15%) and gastrointestinal (up to 20%) reactions that lead to ticlopidine treatment cessation. Besides that lethal thrombocytopenic purpura cases are known [Bennett C., Weinberg P., Rozenberg-Ben-Dror K., et al. Thrombocytopenic purpura associated with ticlopidine. Ann Intern Med 1998; 128: 541-44].

Clopidogrel, according to CAPRIE [Lancet. 1996. V. 348. P. 1329-39], is more effective than aspirin in many cases of long-term treatment of patients with high risk of ischemic occurrences. Its advantages are better tolerance compared to ticlopidine, including lower frequency of hematological complications, faster therapeutic effect onset associated with stress dosing (300 and 600 mg), compatibility with majority of drugs used in cardiology. Clopidogrel disadvantages are resistance of patients with CYP450 polymorphism, especially 2C19 (up to 14% of population) [JACC. 2007. V. 49. P. 1505; FDA Drug Safety Communication. Mar. 12, 2010], considerable efficiency reduction when the drug is used together with proton pump inhibitors—omeprazole, rabeprazole [FDA Public-health advisory: Updated safety information about a drug interaction between clopidogrel bisulfate (marketed as Plavix) and omeprazole (marketed as Prilosec and Prilosec OTC). Nov. 17, 2009], suboptimal drug reaction of the patients with acute coronary syndrome, diabetes, and metabolic syndrome [JACC. 2007. V. 49. P. 1505].

Tikagrelor features relatively quick therapeutic effect onset and pronounced inhibition of thrombocyte aggregation activity. Tikagrelor treatment, compared to clopidogrel one, reduces the frequency of death caused by vascular pathologies, myocardial infarction and strokes with no increase of overall occurrence of large-scale bleedings, but with increase of bleeding occurrences that are not associated with invasive procedures. This is significant disadvantage of the drug that restricts its use [N. Engl. J. Med. 2009. V. 361. N11. P. 1045-57].

Likewise direct thrombin inhibitors—gatrans are used in clinical practice [Am. Heart J. 2009. V. 157. P. 805-810]. Dabigatran shows decrease in stroke risk (including hemorrhagic one), bleeding occurrences (including life threatening and intracranial ones), it also shows decrease in deaths caused by vascular incidents. The drug therapy does not require monitoring [N. Engl. J. Med. 2009. V. 361. N12. P. 1139-1151]. Significant disadvantages of this drug group representatives are hepatotoxicity, intragastric bleedings [NHS. 2009. N8], and also the lack of combined antiaggregant, anticoagulant, and vasodilatory action on the body.

The most similar drugs to the claimed invention in respect to achieved effects are thromboxane blockers—ridogrel, ozagrel, pirmagrel. They have antihypertensive and vasodilator properties. The drugs are safe and effective in case of myocardial infarction [Cardiovascular Drug Reviews. 2008. V18. N3. P. 222-231], and are capable to relieve bronchospasm [Life Science. 1997. V. 60. N18. P. 1583-88].

The disadvantage of this drugs group is low efficiency at oral introduction.

The aim that has been achieved by the authors is the creation of more effective and safe substances that possess combined antiaggregant, anticoagulant and vasodilator action on the body.

BRIEF SUMMARY OF THE INVENTION

The technical result has been achieved by application of N,N'-substituted piperazines with a general formula:

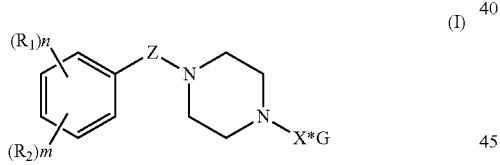

as a drug possessing combined antiaggregant, anticoagulant and vasodilator activity, where $R^1$, $R^2$: linear or branched alkyl ($C_1 \div C_4$), linear or branched alkoxy ($C_1 \div C_4$), $CH_3C(=O)O$, halogen; n=1÷5; m=0÷3; Z=$CH_2$, C=O, $SO_2$;

X: C(=NH)$NH_2$, C(=NH)NHC(=NH)$NH_2$, $CH_2$(CHR$^3$)p$CH_2SO_3H$, where $R^3$=H, OH, $CH_3C(=O)O$, $OSO_3H$; p=0÷1; G: low molecular weight organic or mineral acid, sodium, potassium, ammonium cations or water.

Organic acids with carbon chain length $C_2$-$C_4$ are usually used as a low molecular organic acid like acetic, succinic, fumaric acids, etc. The nature of organic acid does not influence much on pharmacological properties of compound (1).

The mentioned compounds can be used in their pure form or in the form of solvates or pharmaceutically acceptable salts.

At present substituted nitrogen containing heterocyclic compounds are known as substances perspective in antiplatelet therapy.

Thus U.S. Pat. No. 4,370,330 proposes the new N-trimethoxy-benzylpiperazines and pharmaceutically accepted salts thereof with general formula:

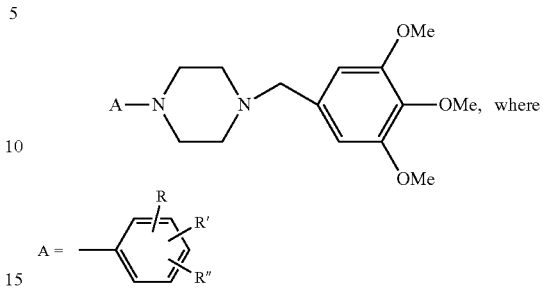

R: $CF_3$, OH, $NO_2$, halogen, alkyl- or alkoxy-; R': H, $CF_3$, halogen, alkyl- or alkoxy-substituent; R": H or alkoxy-substituent for a stimulation of blood circulation.

U.S. Pat. No. 4,574,156 claims polymethoxybenzylpiperazine derivatives with general formula:

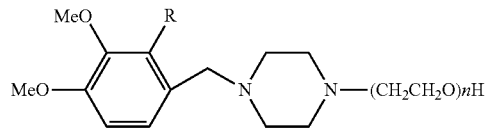

where R: H; OMe; n=2÷5 as agents enhancing blood circulation.

U.S. Pat. No. 4,368,199 proposes the use of 3,4,5-trimethoxycinnamoylpiperazine derivatives with general formula:

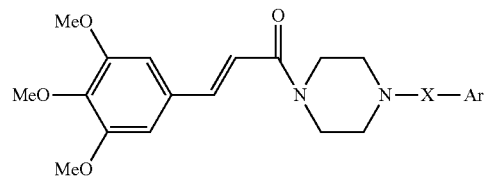

where X: —$(CH_2)_n$, n=1÷3 or —$CH_2$—CO—, n=1, 2; Ar: substituted phenyl- or phenyldioxoalanyl-radicals, etc. for the treatment of vascular and cardiac insufficiency.

EU Pat. 284 359 describes 1,4-disubstituted piperazines and salts thereof with general formula:

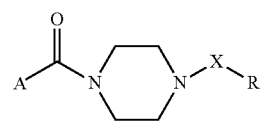

where A: pentalenyl-, indenyl-, indanyl-, naphthyl-, azulenyl- etc. radicals; R: 1÷5 alkoxy-groups substituted phenyl-radical, X: $CH_2$, CO or thiocarbonyl; m=2, 3. Generally this patent describes substituted 3,4,5-trimethoxybenzyl- и 3,4,5-trimethoxybenzoylpiperazines and synthesis thereof comprising the reaction of intermediate compounds with acid having general formula A-COOH or acid halogenide having general formula A-COW, where A: as listed above, W: halogen. These compounds or salts thereof can be used as a part of pharmaceutical compositions for thrombocyte activation factor inhibition and as antiaggregants.

N,N'-substituted piperazines with general formula:

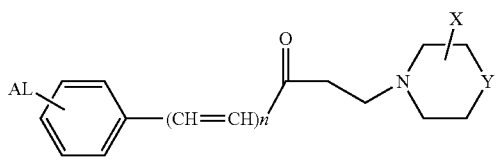

where AL: H, OH, halogen, CN, alkoxy, etc.; n=0÷2; Y: C, N, O; X: H, alkyl, COOR etc.; are used for the therapy and prophylaxis of vascular inflammations and thrombosis (EU Pat. 1 783 115).

Substituted N-benzylpiperidineamides, pharmaceutically acceptable salts thereof or hydrates are used for the heart rate regulation (EU Pat. 416 581, U.S. Pat. No. 5,210,090):

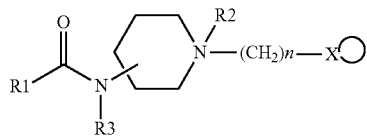

where $R^1$: benzofuranyl-radical; n=0÷10; $R^2$: H, alkyl, O; $R^3$: H, carboxyalkyl; X: H, pyridinyl, phenyl (mono- and polysubstituted by alkyl, halogen, alkoxy substituents).

The compounds with general formula:

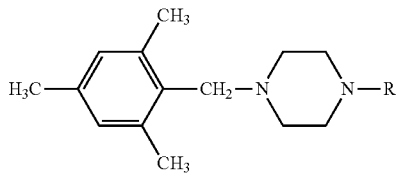

where R-methyl and

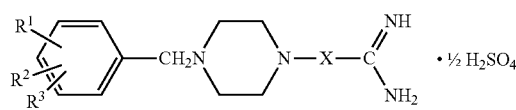

where $R^1$, $R^2$, $R^3$—H, $OCH_3$, $SCH_3$, $C_6H_5$, halogen, phenylthio-, and at least one of the listed radicals is H are known as a substances with hypotensive action (M. Protiva et all. Collection Czechoslov. Chem. Commun. Vol. 41, p. 1035-1041 (1976); CS 151752. 15 Jan. 1974).

The latter of the compounds is synthesized by the addition of S-methylisothiocarbamide sulfate to boiling solution of the compound

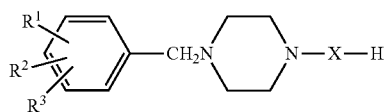

where X, $R^1$, $R^2$, $R^3$ are the same as in the target compound.

The general disadvantage of the described above compounds is the limited variety of actions on the body, since the publications lack the data confirming that corresponding compounds have combined antiaggregant, anticoagulant and vasodilator properties.

The closest compound in respect to the chemical structure of the claimed compounds is the one with general formula (M. Protiva et all. Collection Czechoslov. Chem. Commun. Vol. 40, p. 3904-3923(1975):

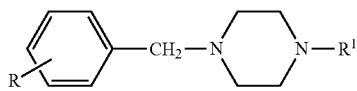

where R, $R^1$=H, $CH_3$, F, $NO_2$, Cl, $OCH_3$, $SCH_3$

However this compound has marked out finite number of possible applications (as a substance with hypotensive action) together with substantial difference in the structure with the claimed ones.

The outlined publication analysis revealed the presence of broad spectrum of biological activity, that is inherent to N,N'-substituted piperazines, and also that compounds exerting influence on haemostasis system are underinvestigated. This makes the more in-depth study of N,N'-substituted piperazines very essential.

In this context together with the aim of effective and safe drug development it becomes attractive to create a new derivatives of N,N'-substituted piperazines having combined antiaggregant, anticoagulant, and vasodilator activity, high safety, perspective in a treatment of haemostasis system diseases.

PREFERRED EMBODIMENTS OF THE INVENTION

To achieve this goal a novel N,N'-substituted piperazines were produced, which biological testing demonstrated their high efficiency.

The created compounds can be divided in two groups with general formulae (II) and (III).

The first group includes N,N'-substituted piperazines with general formula (II):

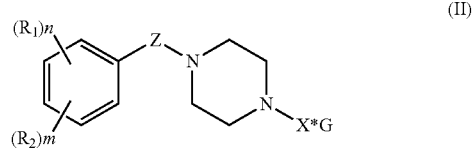

where $R^1$, $R^2$: linear or branched alkyl ($C_1$÷$C_4$), linear or branched alkoxy ($C_1$÷$C_4$), $CH_3C(=O)O$, halogen; n=1÷5; m=0÷3; Z=$CH_2$, C=O, $SO_2$; X: C(=NH)$NH_2$, C(=NH)NHC(=NH)$NH_2$, G: low molecular weight organic or mineral acid.

Hydrates or pharmaceutically acceptable salts thereof can be used for the same purposes instead of the mentioned compounds.

These compounds are synthesized by reaction of N-substituted piperazines with general formula (IV):

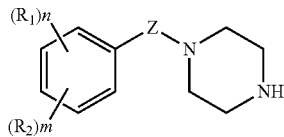

(IV)

where $R^1$, $R^2$: linear or branched alkyl ($C_1 \div C_4$), linear or branched alkoxy ($C_1 \div C_4$), $CH_3C(=O)O$, halogen; $n=1\div 5$; $m=0\div 3$; $Z=CH_2$, $C=O$, $SO_2$;
with carboxamidating agents or salts thereof in organic solvents or in water in the presence of bases.

The process is carried out at room or elevated temperature. The compounds out of the following list can be used as carboxamidating agents: 1H-pyrazole-1-carboxamidine or dicyandiamide, for example, 1H-benzotriazole-1-carboxamidine, 1H-pyrazole-1-carboxamidine, 3,5-dimethyl-1H-pyrazole-1-carboxamidine, dicyandiamide or compounds producing aforementioned ones as a result of hydrolysis, for example dicyandiamide salts, 1H-pyrazole-1-carboxamidine salts. Lower aliphatic alcohols, acetonitrile, tetrahydrofurane, dimethylformamide, dimethylsulfoxide, dichloromethane or mixtures thereof can be used as organic solvents, sodium or potassium hydroxides, carbonates or hydrocarbonates thereof—as the bases. It is reasonable to carry out the reaction at pH values not exceeding 9±0.5, to achieve optimal yields of N,N'-substituted piperazines with formula (II);

The second group (variant 2) includes N,N'-substituted piperazines with general formula (III):

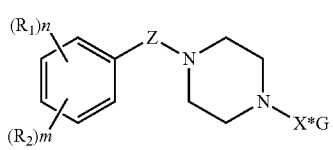

(III)

where $R^1$, $R^2$: linear or branched alkyl ($C_1 \div C_4$), linear or branched alkoxy ($C_1 \div C_4$), $CH_3C(=O)O$, halogen; $n=1\div 5$; $m=0\div 3$; $Z=CH_2$, $C=O$, $SO_2$;
X: $CH_2(CHR^3)pCH_2SO_3H$, where $R^3=H$, OH, $CH_3C(=O)O$, $OSO_3H$; $p=0\div 1$; G—low molecular weight organic or mineral acid, sodium, potassium, ammonium cations or water.

Hydrates or pharmaceutically acceptable salts thereof can be used for the same purposes instead of the mentioned compounds.

The method of synthesis of these compounds is based on the reaction of N-substituted piperazines with general formula (V), and also hydrates or salts thereof:

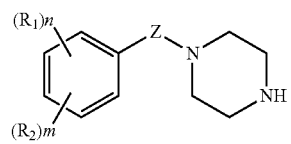

(V)

where $R^1$, $R^2$: linear or branched alkyl ($C_1 \div C_4$), linear or branched alkoxy ($C_1 \div C_4$), $CH_3C(=O)O$, halogen; $n=1\div 5$; $m=0\div 3$; $Z=CH_2$, $C=O$, $SO_2$;
with halogenalkylsulfonic acids or salts thereof in organic solvents or in water in the presence of bases.

The process is carried out at room or elevated temperature. 2-bromoethanesulfonic acid, 2-hydroxy-3-chloropropanesulfonic acid or salts thereof can be used as halogenalkylsulfonic acids. Lower aliphatic alcohols, acetonitrile, tetrahydrofurane, dimethylformamide, dimethylsulfoxide, dichloromethane or mixtures thereof can be used as organic solvents, sodium or potassium hydroxides, their carbonates or hydrocarbonates, triethylamine—as the bases. It is reasonable to carry out the reaction at pH values not exceeding 9±0.5, to achieve optimal yields of N,N'-substituted piperazines with formula (III).

After the reaction completed the isolation of the targeted compound from the reaction mixture is performed by traditional methods of organic synthesis. The choice between solvent evaporation, recrystallization, reprecipitation, chromatography is governed by the mixture composition. The purity of synthesized compounds according to RP-HPLC method was greater than 98%.

The control of the reaction progress as well as target compounds purity evaluation are carried out by RP-HPLC method using Alliance chromatograph (Waters), Zorbax Eclipse C18, 3.5 m, 3*100 mm column (Agilent Technologies), the eluent was the mixture of buffer solution containing 0.01 M sodium octanesulfonate and 0.02 M sodium dihydrophosphate (pH=3.0) with acetonitrile, detection wavelength was 230 nm.

The structure of synthesized compounds was confirmed by the data of $^1H$, $^{13}C$ NMR spectroscopy, mass spectroscopy, elemental analysis. Elemental analysis was carried out on Leco-932 C, H, N, S-analyzer (Leco Corporation).

Molar mass determination was done by mass spectroscopy method on MX-5303 time-of-flight mass-reflectron with "Electrospray" type of ion source.

It was shown in the course of pharmacological and biological investigations that synthesized N,N'-substituted piperazines have good solubility in water, wider therapeutic range and high safety compared to known analogs (derivatives of nitrogen containing heterocyclic compounds and aspirin). These factors allow the wide use of the invented N,N'-substituted piperazines as antiaggregants and substances exerting influence on haemostasis system.

Particularly, the carried out studies of therapy of haemostasis system pathologies showed that introduction of N,N'-substituted piperazines into the body with dosage of 0.005 mmol/kg and higher results in reduction of pathological thrombocyte aggregation, has positive effect on fibrinolysis system, provides vessels vasodilation.

N,N'-Substituted piperazines can be introduced into the body as a part of compositions containing the mixture of physiologically active (functional) compound with excipients. The latter ones are the substances permitted by Pharmacopoeia that improve synthesis, storage or treatment conditions, for example solvents, fillers, scents, flavorings, stabilizers, etc.

Antiaggregant, antithrombotic properties of N,N'-substituted piperazines are proved by the examples shown below.

INDUSTRIAL APPLICABILITY

Example 1

Synthesis of 4-(3,4,5-trimethoxybenzoyl)piperazine-1-carboximidamide fumarate hemihydrate

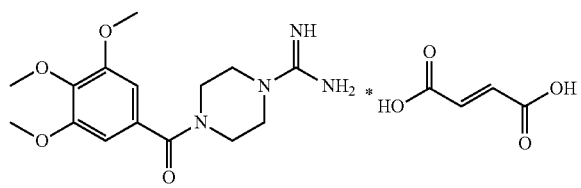 [SMILES: COc1cc(C(=O)N2CCN(C(=N)N)CC2)cc(OC)c1OC ; O=C(O)/C=C/C(=O)O]

1) Synthesis of 3,4,5-trimethoxybenzoyl chloride

In 100 ml one necked flask equipped with reflux condenser and gas outlet tube placed in NaOH solution, 20 g (94 mmol) of 3,4,5-trimethoxybenzoic acid and 45 ml of abs. benzene are placed. Then 0.5 ml of DMFA and 10.8 ml (150 mmol) of thionyl chloride are added. After the end of gas evolution the mixture is refluxed for 2 h. The solution is cooled down to 20° C., poured into the glass with 50 ml of hexane. The precipitated white crystals of the product are filtered off. The filtrate is evaporated in vacuum up to ⅓ of the initial volume at 50° C. The second portion of the product is separated upon cooling down, it is filtered off and combined with the first one. The product is dried in vacuum at 50÷60° C. for 1 h.

Yield of 3,4,5-trimethoxybenzoyl chloride—19.6 g (90%), m. p. 77° C.

2) Synthesis of 1-(3,4,5-trimethoxybenzoyl)piperazine hydrochloride

In 500 ml three necked flask, equipped with mechanical stirrer, dropping funnel and thermometer, 20.0 g (232 mmol) of piperazine, 50 ml of acetic acid and 60 ml of water are placed. The solution of 13 g (56 mmol) of 3,4,5-trimethoxybenzoyl chloride in 15 ml of THF is added dropwise to this mixture for 20 min, maintaining the temperature of reaction mixture at 10÷15° C., then mixture is stirred for 1 h and left overnight. The solution is filtered off, evaporated to dryness in vacuum at 50÷60° C. Then 100 ml of abs. ethanol is added to the residue, the mixture is heated to boiling with stirring. The mixture is cooled down to 20° C. and filtered off. The mother solution is evaporated to dryness in vacuum (~20 mm Hg) at 50÷60° C. Then 100 ml of acetone is added, the mixture is stirred with magnetic stirrer for 30 min at 40÷50° C. The precipitate is filtered off, washed with (2×50 ml) of acetone and dried for 12 h at 40° C.

Yield of 1-(3,4,5-trimethoxybenzoyl)piperazine hydrochloride—7.8 g (44%).

$^1$H NMR spectrum of 1-(3,4,5-trimethoxybenzoyl)piperazine hydrochloride (Brucker 400 MHz; DMSO-$d_6$ solution): 3.35 w.s. (4H; piperazine ring); 3.58-3.78 w. (4H; piperazine ring); 3.69 s. (3H; $CH_3O$); 3.81 s. (6H; $2CH_3O$); 6.75 s. (2H; aromatic); 9.57 w.s. (2H; $NH_2$+).

3a) Synthesis of 4-(3,4,5-trimethoxybenzoyl)piperazine-1-carboximidamide fumarate at pH of reaction mixture 9±0.5

To 4.5 g (14.2 mmol) of 1-(3,4,5-trimethoxybenzoyl)piperazine hydrochloride 1.7 g (16 mmol) of $Na_2CO_3$, 40 ml of water, 2.1 g (14.3 mmol) of 1H-pyrazole-1-carboxamidine monohydrochloride are added, pH of reaction mixture is kept 9±0.5. The mixture is stirred at 20° C. for 24 h. The solution is concentrated in vacuum with heating on the water bath at 50÷80° C. Then 60 ml of abs. ethanol is added to the residue, and the mixture is refluxed for 20 min. The solution is filtered off, filtrate concentrated in vacuum at 50÷80° C. The residue is triturated in a mortar with 50 ml of diethyl ether, then with 50 ml of acetone, then with 50 ml of dichloromethane, dissolved in 50 ml of 1 M NaOH, extracted with (2×50 ml) of dichloromethane. Combined organic extracts are dried over sodium sulfate, concentrated in vacuum at room temperature, dissolved in 100 ml of ethanol. Then 1.65 g (14.2 mmol) of fumaric acid is added, the mixture is boiled for 2 h, the hot solution is filtered off, evaporated up to ¼ of the initial volume, kept at 4° C. for 3 h. The product is separated by filtration, dried in vacuum at 40° C. up to constant mass, recrystallized with isopropanol and dried in vacuum at 40° C. up to constant mass.

Yield of $C_{15}H_{22}N_4O_4*C_4H_4O_4*0.5H_2O$, 4-(3,4,5-trimethoxybenzoyl)piperazine-1-carboximidamide fumarate hemihydrate—2.3 g (35%). Elemental analysis $C_{15}H_{22}N_4O_4*C_4H_4O_4*0.5H_2O$. Calc., %: C, 51.00; N, 6.08; N, 12.52. Found, %: C, 51.08; N, 6.18; N, 12.44. Mass spectrum, base, found: m/z 322.32. Calc.: M 322.36

3b) Synthesis of 4-(3,4,5-trimethoxybenzoyl)piperazine-1-carboximidamide fumarate at pH of reaction mixture 12±0.5

To 4.5 g (14.2 mmol) of 1-(3,4,5-trimethoxybenzoyl)piperazine hydrochloride, 2.07 g (37 mmol) of KOH, 40 ml of water, 2.1 g (14.3 mmol) of 1H-pyrazole-1-carboxamidine monohydrochloride are added, pH of reaction mixture is kept 12±0.5. The mixture is stirred at 20° C. for 24 h. The solution is concentrated in vacuum with heating on the water bath at 50÷80° C. Then 60 ml of abs. ethanol is added to the residue and the mixture is refluxed for 20 min. The solution is filtered off, filtrate concentrated in vacuum at 50÷80° C. The residue is triturated in a mortar with 50 ml of diethyl ether, then with 50 ml of acetone, then with 50 ml of dichloromethane, dissolved in 50 ml of 1 M NaOH, extracted with (2×50 ml) of dichloromethane. Combined organic extracts are dried over sodium sulfate, concentrated in vacuum at room temperature, dissolved in 100 ml of ethanol. Then 1.65 g (14.2 mmol) of fumaric acid is added, the mixture is refluxed for 2 h, the hot solution is filtered off, evaporated up to ¼ of the initial volume, kept at 4° C. for 3 h. The product is separated by filtration, dried in vacuum at 40° C. up to constant mass, recrystallized with isopropanol and dried in vacuum at 40° C. up to constant mass.

Yield of $C_{15}H_{22}N_4O_4*C_4H_4O_4*0.5H_2O$, 4-(3,4,5-trimethoxybenzoyl)piperazine-1-carboximidamide fumarate hemihydrate—1.4 g (21%). Mass spectrum, base, found: m/z 322.32. Calc.: M 322.36

Example 2

Synthesis of N-carbamidoyl-4-(2,3,4-trimethoxybenzoyl)piperazine-1-carboximidamide hydrochloride

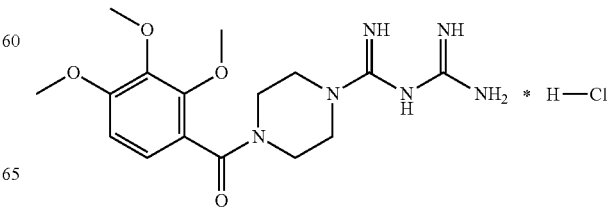

1) Synthesis of 2,3,4-trimethoxybenzoyl chloride

In 100 ml one necked flask, equipped with reflux condenser with gas outlet tube placed in solution of NaOH, 25 g (118 mmol) of 2,3,4-trimethoxybenzoic acid and 50 ml of abs. benzene are placed, then 0.5 ml of DMFA and 10.8 ml (150 mmol) of thionyl chloride are added. After the end of gas evolution the mixture is refluxed for 2 h. The solution is cooled down to 20° C., poured into the glass with 50 ml of hexane. The precipitate is filtered off, the filtrate is evaporated in vacuum up to ⅓ of the initial volume at 50÷80° C. The second portion of the product is separated upon cooling down, which is filtered off and combined with the first one. The product (white powder) is dried in vacuum at 50÷60° C. for 1 h.

Yield of 2,3,4-trimethoxybenzoyl chloride—23.1 g (85%), $T_m$ 42° C.

2) Synthesis of 1-(2,3,4-trimethoxybenzoyl)piperazine hydrochloride

In 500 ml three necked flask, equipped with mechanical stirrer, dropping funnel and thermometer, 30.0 g (348 mmol) of piperazine, 75 ml of acetic acid and 90 ml of water are placed. The solution of 19.5 g (85 mmol) of 2,3,4-trimethoxybenzoyl chloride in 25 ml of THF is added dropwise to this mixture for 30 min, maintaining the reaction mixture temperature at 10÷15° C. The mixture is stirred for 1 h and left overnight. Light yellow solution is evaporated in vacuum to dryness at 50÷60° C. The residue is treated with 450 ml of 2.5 N HCl (1.125 mol) upon cooling with ice and stirred for 15 min. The solution is filtered off. Filtrate is evaporated to dryness in vacuum (~20 mm Hg) at 50÷60° C. The residue is treated with 150 ml of abs. ethanol and heated to boiling with stirring. The mixture is cooled down to 20° C. and piperazine dihydrochloride precipitate is filtered off. The mother solution is evaporated to dryness in vacuum (~20 mm Hg) at 50÷60° C. Then 150 ml of acetone is added to the residue and stirred with magnetic stirrer for 30 min at 40÷50° C. The precipitate is filtered off, washed with (2×50 ml) of acetone and dried for 12 h at 40° C.

Yield of 1-(2,3,4-trimethoxybenzoyl)piperazine hydrochloride—12.1 g (45%).

3) Synthesis of N-carbamidoyl-4-(2,3,4-trimethoxybenzoyl)piperazine-1-carboximidamide hydrochloride In 100 ml one necked flask 6.3 g (20 mmol) of 1-(2,3,4-trimethoxybenzoyl)piperazine hydrochloride, 1.77 g (21 mmol) of dicyandiamide and 50 ml of 1-butanol are added. The mixture is refluxed for 10 h, concentrated in vacuum at 50÷80° C. Then 100 ml of ethanol is added to the residue and the mixture is refluxed for 0.5 h. The hot mixture is filtered off, the precipitate is dried at 45° C. for 2 days.

Yield of $C_{16}H_{24}N_6O_4$*HCl, N-carbamidoyl-4-(2,3,4-trimethoxybenzoyl)piperazine-1-carboximidamide hydrochloride—4.3 g (53%). Elemental analysis $C_{16}H_{24}N_6O_4$*HCl. Calc., %: C, 47.94; H, 6.29; N, 20.96. Found, %: C, 48.63; H, 6.47; N, 21.03. Mass spectrum, base, found: m/z 364.38. Calc.: M 364.40.

$^1$H NMR spectrum of N-carbamidoyl-4-(2,3,4-trimethoxybenzoyl)piperazine-1-carboximidamide hydrochloride (Brucker 400 MHz; DMSO-$d_6$ solution): 3.17-3.70 w. singlets (8H; piperazine ring); 3.75 s. (3H; $CH_3O$); 3.76 s. (3H; $CH_3O$); 3.80 s. (3H; $CH_3O$); 6.83 s. and 6.91 s. (1H and 1H; aromatic); 6.98 w.s. $_H$ 7.38 w.s. (4H and 2H; 2NH, $NH_2$ (+), $NH_2$).

Example 3

Synthesis of 3-(1-(2,3,4-trimethoxybenzyl)piperazine-4-yl)-2-hydroxy-1-propanesulfonic acid sodium salt

1). Synthesis of 3-(1-(2,3,4-trimethoxybenzyl)piperazine-4-yl)-2-hydroxy-1-propanesulfonic acid sodium salt at pH of reaction mixture 9±0.5

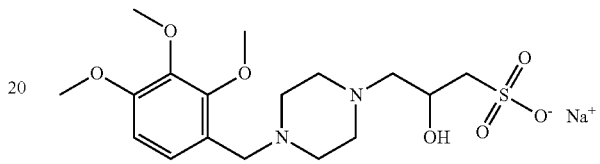

In 100 ml one necked flask 6.8 g (20 mmol) of 1-(2,3,4-trimethoxybenzyl)piperazine dihydrochloride and 30 ml of water are placed, then 5.5 g (65 mmol) of $NaHCO_3$ is added portion wise. After the end of gas evolution the solution of 4.10 g (20 mmol) of 2-hydroxy-3-chloropropanesulfonic acid in 30 ml of water and 0.1 g of potassium iodide are added, pH of reaction mixture is kept 9±0.5.

The mixture is refluxed for 5 h. The solution is evaporated in vacuum (~20 mm Hg) to dryness at 50÷60° C. Then 100 ml of abs. ethanol is added to the residue, and the mixture is refluxed for 0.5 h with stirring. The hot solution is filtered off from inorganic salts and kept for 1 day. White precipitate is filtered off and dried at 45° C. for 2 days.

Yield of $C_{17}H_{27}N_2NaO_7S$, 3-(1-(2,3,4-trimethoxybenzyl)piperazine-4-yl)-2-hydroxy-1-propanesulfonic acid sodium salt—5.2 g (61%).

Elemental analysis $C_{17}H_{27}N_2NaO_7S$. Calc., %: C, 47.88; H, 6.38; N, 6.57. Found, %: C, 47.89; H, 6.11; N, 6.28. Mass spectrum, found: m/z 426.41. Calc.: M 426.46.

$^1$H NMR spectrum of 3-(1-(2,3,4-trimethoxybenzyl)piperazine-4-yl)-2-hydroxy-1-propanesulfonic acid sodium salt (Brucker 400 MHz; DMSO-$d_6$ solution): 2.20-2.44 m. and 2.69 d. (10H; piperazine ring+$CH_2SO_3$); 3.29-3.39 two s. (4H; $2CH_2N$); 3.69-3.79 three s. (9H; $3CH_3O$); 3.94 m. (1H; CH); 4.80 s. (1H; OH); 6.73 d. and 6.93 d. (1H and 1H; benzene ring).

2). Synthesis of 3-(1-(2,3,4-trimethoxybenzyl)piperazine-4-yl)-2-hydroxy-1-propanesulfonic acid sodium salt at pH of reaction mixture 12±0.5

In 100 ml one necked flask the solution of 2.6 g (65 mmol) of NaOH in 30 ml of water is placed, then 6.8 g (20 mmol) of 1-(2,3,4-trimethoxybenzyl)piperazine dihydrochloride, the solution of 4.10 g (20 mmol) of 2-hydroxy-3-chloropropanesulfonic acid in 30 ml of water and 0.1 g of potassium iodide are added, pH of reaction mixture is kept 12±0.5. The mixture is refluxed for 5 h. The solution is evaporated in vacuum (~20 mm Hg) to dryness at 50÷60° C. Then 100 ml of abs. ethanol is added to the residue and the mixture is refluxed for 0.5 h with stirring. The hot solution is filtered off from inorganic salts and kept for 1 day. White precipitate is filtered off and dried at 45° C. for 2 days.

Yield of $C_{17}H_{27}N_2NaO_7S$, 3-(1-(2,3,4-trimethoxybenzyl)-piperazine-4-yl)-2-hydroxy-1-propanesulfonic acid sodium salt 2.7 g (32%).

Mass spectrum, found: m/z 426.41. Calc.: M 426.46.

$^1$H NMR spectrum of 3-(1-(2,3,4-trimethoxybenzyl)piperazine-4-yl)-2-hydroxy-1-propanesulfonic acid sodium salt (Brucker 400 MHz; DMSO-$d_6$ solution): 2.20-2.44 m. and 2.69 d. (10H; piperazine ring+$CH_2SO_3$); 3.29-3.39 two s. (4H; two $CH_2N$); 3.69-3.79 three s. (9H; three $CH_3O$); 3.94 m. (1H; CH); 4.80 s. (1H; OH); 6.73 d. and 6.93 d. (1H and 1H; benzene ring).

Example 4

Synthesis of N-carbamidoyl-4-(2,3,4-trimethoxybenzyl)piperazine-1-carboximidamide hydrochloride

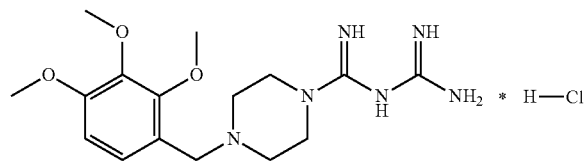

In 100 ml one necked flask 5.05 g (15 mmol) of 1-(2,3,4-trimethoxybenzyl)piperazine monohydrate, 1.51 g (18 mmol) of dicyandiamide and 50 ml of 1-butanol are placed. The mixture is refluxed for 10 h, concentrated in vacuum at 50÷80° C. Then 100 ml of ethanol is added to the residue and the mixture is refluxed for 0.5 h. The hot mixture is filtered off, the filtrate is kept overnight at 15° C. The product (white precipitate) is filtered off, the filtrate is concentrated in vacuum at 50÷80° C. up to one half of the initial volume. The additional amount of the products is separated which is filtered off and combined with the first one. The product is dried at 45° C. for 2 days.

Yield of N-carbamidoyl-4-(2,3,4-trimethoxybenzyl)piperazine carboximidamide—2.5 g (48%). Elemental analysis $C_{16}H_{26}N_6O_3$*HCl. Calc., %: C, 49.68; H, 7.04; N, 21.71. Found, %: C, 49.71; H, 7.05; N, 21.40. Mass spectrum, base, found: m/z 350.48. Calc.: M 350.42.

Example 5

Synthesis of 4-(2,3,4-triethoxybenzyl)piperazine-1-carboximidamide hydrochloride

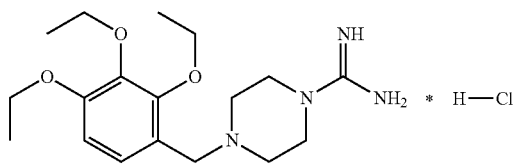

1). Synthesis of 2,3,4-triethoxybenzaldehyde

In 250 ml three necked flask, equipped with reflux condenser, mechanical stirrer, 13.9 g (90 mmol) of 2,3,4-trihydroxybenzaldehyde, 5.6 g (100 mmol) of KOH and 100 ml of dry dimethylformamide are placed at the argon condition. The mixture is stirred for 20 min at the argon condition, then 84 g (43.5 ml, 540 mmol) of ethyliodide is added. The mixture is refluxed at 70÷100° C. with stirring in argon condition for 20 h, concentrated in vacuum at 50÷80° C. to dryness. Then 200 ml of water is added to the residue, the mixture is extracted with (4×100 ml) of dichloromethane. The combined organic fraction is washed with 7% NaOH solution, dried over magnesium sulfate, filtered off. The solvent is evaporated in vacuum at 50÷80° C. The residue is distilled in vacuum, collecting the fraction with b.p. 115-120° C. (0.5 mm Hg).

Yield of 2,3,4-triethoxybenzaldehyde—7.4 g (34%).

2). Synthesis of N-(tert-butyloxycarbonyl)-N'-(2,3,4-triethoxybenzyl) piperazine The synthesis is carried out in argon condition. 1.1 g (5.9 mmol) of N-Boc-piperazine and 1.40 g (5.9 mmol) of 2,3,4-triethoxybenzaldehyde are mixed in 25 ml of dry dichloromethane. After dissolution 2 drops of acetic acid is added, then 2.12 g (10 mmol) of $NaBH(OAc)_3$ is added and the mixture is stirred for 12 h at 20° C. Then 10 ml of 5% $NaHCO_3$ aqueous solution is added dropwise with care to the reaction mixture. The organic layer is separated, washed with 5% $Na_2CO_3$ solution, dried over sodium sulfate, filtered off and concentrated in vacuum at 50÷80° C. The residue (2.2 g of yellowish oil) is used on the next step.

3). Synthesis of N-(2,3,4-triethoxybenzyl)piperazine dihydrochloride

To 2.2 g of N-(tert-butyloxycarbonyl)-N'-(2,3,4-triethoxybenzyl) piperazine 20 ml of 10% HCl and 5 ml of ethanol are added, the mixture is stirred for 5 h at 20° C., evaporated to dryness in vacuum at 50÷80° C. Then 20 ml of dry acetone is added to the residue, the mixture is boiled with stifling for 20 min, cooled down to 10° C. After 1 h the product is filtered off, washed with 10 ml of acetone and dried at the air.

Yield of 1-(2,3,4-triethoxybenzyl)piperazine dihydrochloride 1.2 g (53%).

4). Synthesis of 4-(2,3,4-triethoxybenzyl)piperazine-1-carboximidamide hydrochloride To 1.2 g (3.15 mmol) of 1-(2,3,4-triethoxybenzyl)piperazine dihydrochloride 0.67 g (6.3 mmol) of $Na_2CO_3$ and 20 ml of water are added. Then 0.48 g (3.3 mmol) of 1H-pyrazole-1-carboxamidine monohydrochloride is added and the mixture is stirred at 50° C. for 8 h. The solution is evaporated in vacuum at 50÷80° C. Then 60 ml of dichloromethane is added to the residue and the mixture is refluxed for 20 min. Non-dissolved white precipitate is filtered off. The solution is evaporated in vacuum at 50÷80° C. down to 2 ml volume, then 7 ml of acetone is added and the mixture is heated to boiling. White crystals of the product is precipitated from the solution upon cooling. They are filtered off and dried at 40° C.

Yield of $C_{18}H_{30}N_4O_3$*HCl, 4-(2,3,4-triethoxybenzyl)piperazine-1-carboximidamide hydrochloride—0.6 g (52%). $C_{18}H_{30}N_4O_3$*HCl. Elemental analysis $C_{18}H_{30}N_4O_3$*HCl. Calc., %: C, 55.87; N, 8.08; N, 14.48. Found, %: C, 55.63; N, 8.06; N, 14.34. Mass spectrum, base, found: m/z 350.52. Calc.: M 350.46.

Example 6

Synthesis of 2-(1-(2,3,4-trimethoxybenzyl)piperazine-4-yl-ethanesulfonic acid sodium salt

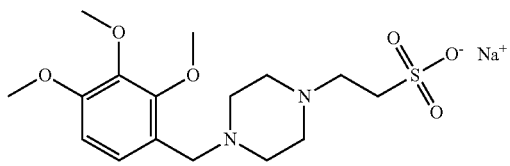

In 200 ml one necked flask 8.5 g (25 mmol) of 1-(2,3,4-trimethoxybenzyl)piperazine dihydrochloride and 30 ml of water are placed. 10 ml (70 mmol) of triethylamine and solution of 5.25 g (25 mmol) of 2-bromoethanesulfonic acid sodium salt in 20 ml of water are added portion wise to this solution. The mixture is refluxed for 2 h. The solution is evaporated in vacuum to dryness at 50÷80° C. The residue (white powder) is dried in vacuum at 50÷60° C., 80 ml of abs. ethanol is added and the mixture is refluxed for 15 min. The hot solution is filtered off, the mother solution is left overnight at room temperature. The precipitate is filtered off and recrystallized with 30 ml of abs. ethanol, then filtered off, dried at 50° C. for 1 day.

Yield of $C_{16}H_{25}N_2NaO_6S$, 2-(1-(2,3,4-trimethoxybenzyl)piperazine-4-yl-ethanesulfonate sodium salt—5.9 g (60%). Elemental analysis $C_{16}H_{25}N_2NaO_6S$. Calc., %: C, 48.48; N, 6.36; N, 7.07. Found, %: C, 48.40; N, 6.34; N, 7.10. Mass spectrum, found: m/z 396.14. Calc.: M 396.43.

$^1$H NMR spectrum 2-(1-(2,3,4-trimethoxybenzyl)piperazine-4-yl-ethanesulfonate sodium salt (Brucker 400 MHz; DMSO-$d_6$ solution): 2.32 m. (10H), piperazine ring; 2.50-2.60, multiplet—N—CH$_2$CH$_2$—SO$_3$; 3.33, singlet, 3CH$_2$; 3.36, singlet—4 protons of piperazine ring; 3.71, 3.74, 3.76 singlets—CH$_3$O; 6.72, doublet—CH; 6.93 doublet—2CH; 6.73 d. and 6.93 d. (1H и 1H; benzene ring).

Example 7

Synthesis of 4-(2,3,4-trimethoxybenzyl)piperazine-1-carboximidamide monohydrate

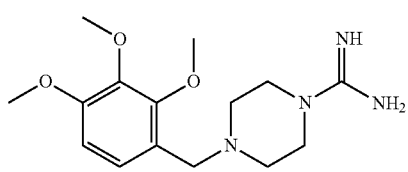 [SMILES: COc1ccc(CN2CCN(C(=N)N)CC2)c(OC)c1OC]

In 100 ml one necked flat-bottom flask 8.5 g (25 mmol) of 1-(2,3,4-trimethoxybenzyl)-piperazine dihydrochloride and 50 ml of water are placed. Then 5.3 g (50 mmol) of Na$_2$CO$_3$ is added portion wise with stirring. Slight gas evolution is observed. To clear solution 3.75 g (25.5 mmol) of 1-N-pyrazole-1-carboxamidine hydrochloride is added in one portion, the suspension is stirred at room temperature for 2 h. The yellow solution is kept at 10° C. for 3 days, then evaporated to dryness in vacuum at 50÷60° C. Then 100 ml of methylene chloride is added to the residue and the mixture is refluxed for 30 min. The white crystalline precipitated is filtered off and discarded (inorganic salts). The solution is dried over sodium sulfate, filtered off and concentrated in vacuum at 50÷80° C. The residue (viscous oil) is kept in vacuum (10 mm Hg) at 60° C. for 1 h, then 50 ml of hot dry acetone is added and the mixture is refluxed on the water bath for 20 min. The white precipitate is filtered off, the filtrate and the rest of viscous oil is continued to reflux with stirring on the water bath for 20 min. The white precipitate is filtered off again and combined with the first portion. The resulted product is treated with 40 ml of 1 M Na$_2$CO$_3$ solution, extracted with (3×20 ml) of chloroform. The chloroform solution is washed with 20 ml of water, dried over anhydrous sodium sulfate, and concentrated in vacuum at 35° C.

Yield of $C_{15}H_{24}N_4O_3*H_2O$, 4-(2,3,4-trimethoxybenzyl)piperazine-1-carboximidamide monohydrate—6.1 g (73%).

Elemental analysis $C_{15}H_{24}N_4O_3*H_2O$. Calc., %: C, 55.20; N, 8.03; N, 17.17. Found, %: C, 55.11; N, 8.06; N, 17.21. Mass spectrum, base, found: m/z 308.42. Calc.: M 308.38.

Example 8

Synthesis of 4-(2,3,4-trimethoxybenzyl)piperazine-1-carboximidamide fumarate

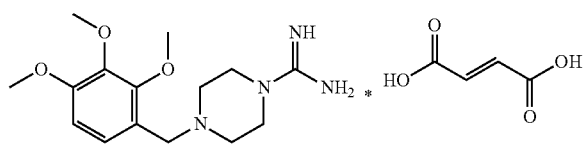 [SMILES: COc1ccc(CN2CCN(C(=N)N)CC2)c(OC)c1OC ; O=C(O)/C=C/C(=O)O]

5.2 g (15 mmol) of 4-(2,3,4-trimethoxybenzyl)piperazine-1-carboximidamide hydrochloride is dissolved in 50 ml of 1 M NaOH, the solution in extracted with (2×50 ml) of dichloromethane. The combined organic extracts are dried over sodium sulfate, concentrated in vacuum at room temperature, and dissolved in 100 ml of ethanol. To this solution 1.7 g (15 mmol) of fumaric acid is added, and the mixture is boiled for 2 h. The hot solution is filtered off, the filtrate is evaporated up to ¼ of the initial volume and kept at 4° C. for 3 h. The product is separated by filtration, dried in vacuum at 40° C. up to constant mass, recrystallized with isopropanol and dried in vacuum at 40° C. up to constant mass.

Yield of $C_{15}H_{24}N_4O_3*C_4H_4O_4$, 4-(2,3,4-trimethoxybenzyl)piperazine-1-carboximidamide fumarate—2.2 g (35%). Elemental analysis $C_{15}H_{24}N_4O_3*C_4H_4O_4$. Calc., %: C, 53.77; N, 6.65; N, 13.20. Found, %: C, 53.52; N, 6.63; N, 13.25. Mass spectrum, base, found: m/z 308.42. Calc.: M 308.38.

$^1$H NMR spectrum (Brucker 400 MHz; CDCl$_3$ solution): 2.47, wide singlet—4 protons of piperazine ring; 3.42, singlet—3CH$_2$; 3.51, wide singlet—4 protons of piperazine ring; 3.79, singlet—CH$_3$O; 3.80, singlet—2CH$_3$O; 6.58, doublet—CH; 6.89, doublet—2CH; 7.27-7.37, wide singlet—4NH+5NH$_2$+water.

Example 9

Synthesis of 3-(1-(3-tert-butyl-4-methoxybenzyl)piperazine-4-yl)-2-hydroxy-1-propanesulfonic acid potassium salt

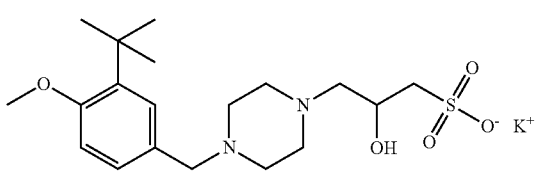

1). Synthesis of N-(tert-butyloxycarbonyl)-N'-(3-tert-butyl-4-methoxybenzyl)-piperazine The synthesis is carried out in argon condition. 2 g (10.7 mmol) of N-Boc-piperazine and 2.06 g (10.7 mmol) of 3-tert-butyl-4-methoxybenzaldehyde are mixed in 30 ml of dry dichloromethane. After dissolution 2 drops of acetic acid is added, then 4.24 g (20 mmol) of NaBH(OAc)$_3$ is added and the mixture is stirred for 12 h at 20° C. Then 20 ml of 5% NaHCO$_3$ aqueous solution is added dropwise with care to the reaction mixture. The organic layer is separated, washed with 5% Na$_2$CO$_3$ solution, dried over sodium sulfate, filtered off and concentrated in vacuum at 50÷80° C. The residue (3.5 g of yellow oil) is used on the next step.

2). Synthesis of (3-tert-butyl-4-methoxybenzyl)piperazine dihydrochloride

To 3.5 g of N-(tert-butyloxycarbonyl)-N'-(3-tert-butyl-4-methoxy-benzyl)piperazine 30 ml of 10% HCl and 5 ml of ethanol are added, the mixture is stirred for 5 h at 20° C., and evaporated to dryness in vacuum at 50÷80° C. Then 20 ml of dry acetone is added to the residue, the mixture is boiled with stifling for 20 min, then cooled down to 10° C. After 1 h the product is filtered off, washed with 10 ml of acetone and dried at the air. Yield of (3-tert-butyl-4-methoxybenzyl)piperazine dihydrochloride—2.2 g (68%).

3). Synthesis of potassium salt of 3-(1-(3-tert-butyl-4-methoxybenzyl)piperazine-4-yl)-2-hydroxy-1-propanesulfonic acid In 100 ml one necked flask 2.2 g (6.6 mmol) of (3-tert-butyl-4-methoxybenzyl)piperazine dihydrochloride and 30 ml of water are placed, then 5 g of KHCO$_3$ is added portion wise. After the end of gas evolution, the solution of 1.4 g (6.6 mmol) of 2-hydroxy-3-chloropropanesulfonic acid sodium salt in 30 ml of water and 0.1 g of potassium iodide are added. The mixture is refluxed for 5 h. The solution is evaporated in vacuum (~20 mm Hg) to dryness at 50÷60° C. The residue is treated with 50 ml of abs. ethanol and the mixture is refluxed with stirring for 1 h. The hot solution is filtered off from inorganic salts and kept for 1 day. White precipitate is filtered off and dried at 45° C. for 2 days.

Yield of C$_{19}$H$_{31}$KN$_2$O$_5$S, (3-tert-butyl-4-methoxybenzyl)-piperazine-4-yl)-2-hydroxy-1-propanesulfonic acid potassium salt-1.3 g (45%).

Elemental analysis C$_{19}$H$_{31}$KN$_2$O$_5$S. Calc., %: C, 52.03; H, 7.12; N, 6.39. Found, %: C, 51.91; H, 7.11; N, 6.41. Mass spectrum, found: m/z 438.54. Calc.: M 438.40.

Example 10

Synthesis of 4-(3,5-dimethoxy-4-ethoxybenzyl)piperazine-1-carboximidamide hydrochloride

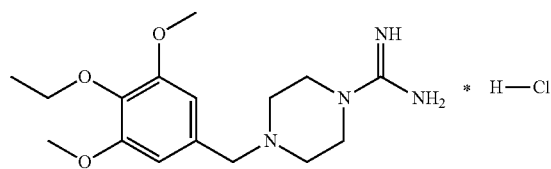 [SMILES: CCOc1c(OC)cc(CN2CCN(C(=N)N)CC2)cc1OC ; Cl]

1). Synthesis of 3,5-dimethoxy-4-ethoxybenzaldehyde

In 250 ml three necked flask, equipped with reflux condenser, mechanical stirrer, 18.2 g (100 mmol) of 3,5-dimethoxy-4-hydroxybenzaldehyde, 28 g (200 mmol) of dry K$_2$CO$_3$ and 100 ml of dry dimethylformamide are placed in argon condition. The mixture is stirred for 20 min in argon condition, then 42 g (21.7 ml, 270 mmol) of ethyliodide is added. The mixture is refluxed in argon condition with stirring for 20 h at 70÷100° C., and concentrated in vacuum at 50÷80° C. to dryness. Then 200 ml of water is added to the residue and the mixture is extracted with (4×100 ml) of methylene chloride. The combined organic fraction is washed with 7% NaOH solution, dried over magnesium sulfate, filtered off, concentrated in vacuum at 50÷80° C. The residue (20 g of oil) is used on the next step without further purification.

2). Synthesis of N-(tert-butyloxycarbonyl)-N'-(3,5-dimethoxy-4-ethoxybenzyl)-piperazine The synthesis is carried out in argon condition. 2.2 g (11.8 mmol) of N-Boc-piperazine and 2.5 g (11.8 mmol) of 3,5-dimethoxy-4-ethoxybenzaldehyde are mixed in 50 ml of dry of dichloromethane. After dissolution 2 drops of acetic acid is added, then 4.25 g (20 mmol) of NaBH(OAc)$_3$ is added and the mixture is stirred for 12 h at 20° C. Then 20 ml of 5% NaHCO$_3$ aqueous solution is added dropwise with care to the reaction mixture. The organic layer is separated, washed with 5% Na$_2$CO$_3$ solution, dried over sodium sulfate, filtered off, concentrated in vacuum at 50÷80° C. The residue (4.1 g of oil) is used on the next step.

3). Synthesis of N-(3,5-dimethoxy-4-ethoxybenzyl)piperazine dihydrochloride

To 4.1 g of N-(tert-butyloxycarbonyl)-N'-(3,5-dimethoxy-4-ethoxy-benzyl)piperazine 40 ml of 10% HCl and 10 ml of ethanol are added, the mixture is stirred for 5 h at 20° C., and evaporated to dryness in vacuum at 50÷80° C. Then 30 ml of dry acetone is added to the residue, the mixture is boiled with stifling for 20 min, cooled down to 10° C. White precipitate is filtered off in an hour, washed with 10 ml of acetone and dried at the air. The product (2 g) is used on the next step without further purification.

4). Synthesis of 4-(3,5-dimethoxy-4-ethoxybenzyl)piperazine-1-carboximidamide hydrochloride To 1.3 g (3.15 mmol) of N-(3,5-dimethoxy-4-ethoxybenzyl)piperazine dihydrochloride 0.67 g (6.3 mmol) of Na$_2$CO$_3$ and 20 ml of water are added, then 0.48 g (3.3 mmol) of 1H-pyrazole-1-carboxamidine monohydrochloride is added and the mixture is stirred at 20° C. for 24 h. The solution is evaporated in vacuum at 50÷80° C. Then 60 ml of methylene chloride is added to the residue, the mixture is refluxed for 20 min. The solution is filtered off, evaporated in vacuum down to 2 ml of volume at 50÷80° C. Then 7 ml of acetone is added and the mixture is heated to boiling. White crystals of the product is precipitated upon cooling from solution. The product is filtered off and dried at 40° C.

Yield of C$_{16}$H$_{26}$N$_4$O$_3$*HCl, 4-(3,5-dimethoxy-4-ethoxybenzyl)piperazine-1-carboximidamide hydrochloride—0.8 g (56%). Elemental analysis C$_{16}$H$_{26}$N$_4$O$_3$*HCl. Calc., %: C, 53.55; N, 7.58; N, 15.61. Found, %: C, 53.52; N, 7.46; N, 15.69. Mass spectrum, base, found: m/z 322.38. Calc.: M 322.40.

Example 11

Synthesis of 4-(4-Acetyloxy-3,5-dimethoxybenzoyl) piperazine-1-carboximidamide hydrochloride

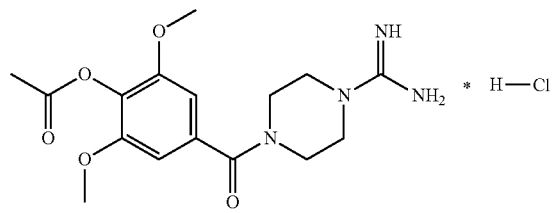 [SMILES: COc1cc(C(=O)N2CCN(C(=N)N)CC2)cc(OC)c1OC(C)=O ; Cl]

1). Synthesis of 1-(4-acetyloxy-3,5-dimethoxybenzoyl)piperazine hydrochloride

In 500 ml three necked flask, equipped with mechanical stirrer, dropping funnel and thermometer, 20.0 g (232 mmol) of piperazine, 50 ml of acetic acid and 60 ml of water are placed. Then the solution of 13 g (50 mmol) of 4-acetyloxy-3,5-dimethoxybenzoyl chloride in 15 ml of THF is added dropwise for 20 min, maintaining the reaction mixture temperature at 10÷15° C. The mixture is stirred for 1 h and left overnight. The solution is evaporated in vacuum to dryness at 50÷60° C. The residue is treated with 300 ml (750 mmol) of 2.5 N HCl with ice cooling, the mixture is stirred for 15 min. The solution is filtered off, the mother solution is evaporated to dryness in vacuum (~20 mm Hg) at 50÷60° C. The residue is treated with 100 ml of abs. ethanol and the mixture is heated to boiling with stirring. The mixture is cooled to 20° C. and filtered off. The mother solution is evaporated to dryness in vacuum (~20 mm Hg) at 50÷60° C. Then 100 ml of acetone is added to the residue and the mixture is stirred with magnetic stirrer for 30 min at 40÷50° C. White precipitate is filtered off, washed with (2×50 ml) of acetone, and dried for 12 h at 40° C.

Yield of 1-(4-acetyloxy-3,5-dimethoxybenzoyl)piperazine hydrochloride—7.6 g (44%).

2). Synthesis of 4-(4-acetyloxy-3,5-dimethoxybenzoyl)piperazine-1-carboximidamide hydrochloride To 4.52 g (13.1 mmol) of 1-(4-acetyloxy-3,5-dimethoxybenzoyl)piperazine hydrochloride 1.6 g (14.8 mmol) of $Na_2CO_3$ and 40 ml of water are added, then 1.92 g (13.1 mmol) of 1H-pyrazole-1-carboxamidine hydrochloride is added. The mixture is stirred at 30° C. for 24 h. The solution is evaporated in vacuum at 50÷80° C. Then 60 ml of isopropanol is added to the residue and the mixture is refluxed for 20 min. The solution is filtered off, the mother solution is concentrated in vacuum at 50÷80° C. The residue is triturated in a mortar with 50 ml of diethyl ether, then with 50 ml of acetone, then with 50 ml of dichloromethane and dried. The resulted product (white powder) is recrystallized with isopropanol, dried for 12 h at 40° C.

Yield of $C_{16}H_{22}N_4O_5$*HCl, 4-(4-acetoxy-3,5-dimethoxybenzoyl) piperazine-1-carboximidamide hydrochloride—2.0 g (35%). Elemental analysis $C_{16}H_{22}N_4O_5$*HCl. Calc., %: C, 49.68; N, 5.99; N, 14.48. Found, %: C, 49.79; N, 5.86; N, 14.43. Mass spectrum, base, found: m/z 350.42. Calc.: M 350.36.

Example 12

Synthesis of 4-(4-(2-methylpropyloxy)-3-methoxybenzyl)piperazine-1-carboximidamide hydrochloride

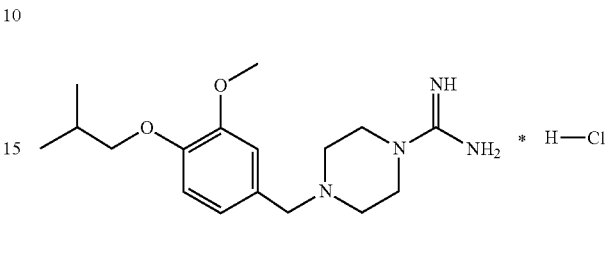

1). Synthesis of 4-(2-methylpropyloxy)-3-methoxybenzaldehyde

In 250 ml three necked flask, equipped with reflux condenser, mechanical stirrer, 30.4 g (200 mmol) of vanillin, 28 g (200 mmol) of dry $K_2CO_3$ and 150 ml of abs. dimethylformamide are placed in the flow of argon. The mixture is stirred for 20 min in argon condition, then 34.3 g (250 mmol) of isobutyl bromide is added. The mixture is refluxed with stirring in argon condition for 20 h at 90÷100° C., and concentrated in vacuum at 50÷80° C. to dryness. Then 200 ml of water is added to the residue, the mixture is extracted with (4×100 ml) of dichloromethane. The combined organic fraction is washed with 7% NaOH solution, dried over magnesium sulfate, filtered off, concentrated in vacuum at 50÷80° C. The residue (15 g of brown oil)-crude 4-(2-methylpropyloxy)-3-methoxybenzaldehyde is used on the next step without further purification.

2). Synthesis of N-(tert-butyloxycarbonyl)-N'-(4-(2-methylpropyloxy)-3-methoxy-benzyl)piperazine The synthesis is carried out in argon condition. 2.2 g (11.8 mmol) of N-Boc-piperazine and 2.5 g (about 12 mmol) of crude 4-(2-methylpropyloxy)-3-methoxybenzaldehyde are mixed in 50 ml of dry of dichloromethane. After dissolution 2 drops of acetic acid is added, then 4.25 g (20 mmol) of $NaBH(OAc)_3$ is added and the mixture is stirred for 12 h at 20° C. Then 20 ml of 5% $NaHCO_3$ aqueous solution is added dropwise with care to the reaction mixture. The organic layer is separated, washed with 5% $Na_2CO_3$ solution, dried over sodium sulfate, filtered off, concentrated in vacuum at 50÷80° C. The residue (3.3 g of oil)-crude N-(tert-butyloxycarbonyl)-N'-(4-(2-methylpropyloxy)-3-methoxybenzyl)piperazine is used on the next step without further purification.

3). Synthesis of N-(4-(2-methylpropyloxy)-3-methoxybenzyl)piperazine dihydrochloride To 3.2 g of crude N-(tert-butyloxycarbonyl)-N'-(4-(2-methylpropyloxy)-3-methoxy-benzyl)piperazine 40 ml of 20% HCl and 10 ml of ethanol are added. The mixture is stirred for 5 h at 20° C. and evaporated to dryness in vacuum at 50÷80° C. Then 30 ml of abs. acetone is added to the residue, and the mixture is boiled with stirring for 20 min, cooled to 10° C. White precipitate is filtered off in an hour, washed with 10 ml of acetone and dried at the air.

The yield of the product (white powder) N-(4-(2-methylpropyloxy)-3-methoxy-benzyl)piperazine dihydrochloride is 2.2 g.

4). Synthesis of 4-(4-(2-methylpropyloxy)-3-methoxybenzyl)piperazine-1-carboximidamide hydrochloride To 1.5 g (4.3 mmol) of N-(4-(2-methylpropyloxy)-3-methoxybenzyl)piperazine dihydrochloride 0.91 g (8.6 mmol) of $Na_2CO_3$ and 20 ml of water are added, then 0.67 g (4.6 mmol) of 1H-pyrazole-1-carboxamidine monohydrochloride is added and the mixture is stirred at 20° C. for 24 h. The solution is evaporated in vacuum at 50÷80° C. Then 60 ml of dichloromethane is added to the residue and the mixture is refluxed for 20 min. The solution is filtered off and evaporated down to 2 ml of volume in vacuum at 50÷80° C. Then 10 ml of acetone is added and the mixture is heated to boiling. White crystals of the product is precipitated upon cooling from solution. The product is filtered off and dried at 40° C.

Yield of $C_{17}H_{28}N_4O_2$*HCl, 4-(4-(2-methylpropyloxy)-3-methoxybenzyl)piperazine-1-carboximidamide hydrochloride—0.7 g (46%). Elemental analysis $C_{17}H_{28}N_4O_2$*HCl. Calc., %: C, 57.21; N, 7.98; N, 15.70. Found, %: C, 57.31; N, 7.92; N, 15.67. Mass spectrum, base, found: m/z 320.48. Calc.: M 320.43.

Example 13

Synthesis of 4-(2,4,5-trichlorophenylsulfonyl)piperazine-1-carboximidamide hydrochloride

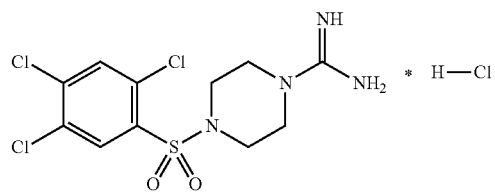 [SMILES: N=C(N)N1CCN(S(=O)(=O)c2cc(Cl)c(Cl)cc2Cl)CC1 ; Cl]

1). Synthesis of 1-(2,4,5-trichlorophenylsulfonyl)piperazine hydrochloride

In 500 ml three necked flask, equipped with mechanical stirrer, dropping funnel and thermometer 22.8 g (200 mmol) of N-formylpiperazine, 25 g (34 ml, 250 mmol) of triethylamine and 100 ml of dichloromethane are placed. Then the solution of 14.0 g (200 mmol) of 2,4,5-trichlorophenylsulfonyl chloride in 100 ml of dichloromethane is added dropwise with stirring for 1 h, maintaining the temperature of reaction mixture at 10÷15° C. (water/ice cooling). The mixture is stirred for 1 h and left overnight at room temperature.

The reaction mixture is poured into the separating funnel with 0.4 l of water. The organic layer is separated, washed with (2×150 ml) of 5% $NaHCO_3$ solution, then with 100 ml of water. The solution in dichloromethane is dried over $Na_2SO_4$, filtered off and the solvent is evaporated in vacuum (~20 mm Hg) with heating on the water bath at 50-60° C. To the resulted residue the solution of 0.5 mol HCl in 200 ml of methanol (obtained by careful addition of 40 g (~0.5 mol) of acetyl chloride to 200 ml of methanol at 10÷15° C.) is added. The mixture is refluxed with stifling for 5 h. White crystalline is precipitated. The mixture is left overnight at room temperature.

The reaction mixture is concentrated in vacuum (~20 mm Hg) with heating on the water bath at 50-60° C. Then 200 ml of water and 50 ml of 20% HCl are added to the residue and the mixture is stirred for 1 h. The non-dissolved gray powder is filtered off. The acidic aqueous solution is concentrated in vacuum (~20 mm Hg) with heating on the water bath at 50-60° C. Then 200 ml of ethanol is added to the residue and the mixture is refluxed for 30 min. White precipitate is filtered off (piperazine dihydrochloride according to $^1$H NMR data). The solution is cooled with ice for 2 h, small white crystals are precipitated, filtered off, dried at the air.

Yield of 1-(2,4,5-trichlorophenylsulfonyl)piperazine hydrochloride as a white powder is 35.1 g—48%.

2). Synthesis of 4-(2,4,5-trichlorophenylsulfonyl)piperazine-1-carboximidamide hydrochloride To 4.94 g (13.5 mmol) of 1-(2,4,5-trichlorophenylsulfonyl)piperazine hydrochloride 1.6 g (14.8 mmol) of $Na_2CO_3$ and 40 ml of water, then 2.05 g (14.0 mmol) of 1H-pyrazole-1-carboxamidine monohydrochloride are added. The mixture is stirred at 20° C. for 48 h. The solution is evaporated in vacuum (~20 mm Hg) with heating on the water bath at 50-60° C. Then 100 ml of abs. ethanol is added to the residue (light yellow mass) and the mixture is refluxed for 20 min. The non-dissolved white solid is filtered off and refluxed with 80 ml of abs. ethanol for 20 min. The non-dissolved white solid (inorganic salts) is filtered off. The combined alcohol solution is evaporated in vacuum (~20 mm Hg) with heating on the water bath at 50-60° C. Then 100 ml of acetone is added to the residue and the mixture is refluxed with magnetic stirring for 1 h. The hot mixture is filtered off, white precipitate is washed with 20 ml of hot acetone. The resulted white powder is dissolved in 100 ml of boiling ethanol, filtered off. After cooling to room temperature the solution is cooled down to 0° C. and kept at that temperature for 2 h. The precipitated crystals are filtered off and dried at the air.

Yield of $C_{11}H_{13}Cl_3N_4O_2S$*HCl, 4-(2,4,5-trichlorophenylsulfonyl)piperazine-1-carboximidamide hydrochloride—2.1 g (42%). Mass spectrum, base, found: m/z 371.52. Calc.: M 371.67.

Example 14

Synthesis of 2-sulfooxy-3-(4-((2,3,4-trimethoxyphenyl)-methyl)piperazine-1-yl)propane-1-sulfonic acid disodium salt monohydrate

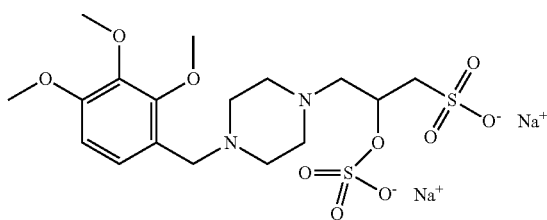 [SMILES: COc1ccc(CN2CCN(CC(CS(=O)(=O)[O-])OS(=O)(=O)[O-])CC2)c(OC)c1OC ; [Na+] ; [Na+]]

In 250 ml three necked flask, equipped with mechanical stirrer, dropping funnel and thermometer 4.3 g (10 mmol) of 3-(1-(2,3,4-trimethoxybenzyl)piperazine-4-yl)-2-hydroxy-1-propanesulfonic acid sodium salt (made according to Example 3) and 60 ml of dichloromethane are placed. Then 1.5 g (15 mmol) of triethylamine is added dropwise at room temperature, the mixture is cooled with ice and the solution of 2.4 g (15 mmol) of pyridine-sulfur trioxide complex in 20 ml of dichloromethane is added dropwise for 20 min, maintaining the reaction mixture temperature at 10÷15° C. Then the mixture is stirred for 2 h at 20° C. Then 5 ml of 3M $Na_2CO_3$ solution (15 mmol) is added dropwise with ice cooling. The mixture is evaporated to dryness in vacuum at 50÷60° C. The residue is treated with 100 ml of ethanol and refluxed with stirring for 0.5 h. The hot mixture is filtered off. The filtrate is concentrated in vacuum (~20 mm Hg) down to ¼ of the initial volume. The precipitate is filtered off, washed with (2×50 ml) of acetone. The white powder is dried for 12 h at 40° C.

Yield of $C_{17}H_{26}N_2O_{10}S_2Na_2*H_2O$, 2-sulfooxy-3-(4-((2,3,4-trimethoxy-phenyl)methyl)piperazine-1-yl)propane-1-sulfonic acid disodium salt monohydrate—2.4 g (44%). Elemental analysis $C_{17}H_{26}N_2O_{10}S_2Na_2*H_2O$. Calc., %: C, 37.36; N, 5.16; N, 5.13. Found, %: C, 37.40; N, 5.18; N, 5.11. Mass spectrum, found: m/z 528.3. Calc.: M 528.50.

Example 15

Synthesis of 2-acetoxy-3-(4-((2,3,4-trimethoxyphenyl)methyl)-piperazine-1-yl)propane-1-sulfonic acid sodium salt monohydrate

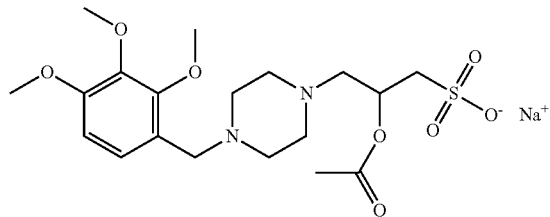 [SMILES: COc1ccc(CN2CCN(CC(CS(=O)(=O)[O-])OC(C)=O)CC2)c(OC)c1OC ; [Na+]]

In 250 ml three necked flask, equipped with mechanical stirrer, dropping funnel and thermometer 4.3 g (10 mmol) of 3-(1-(2,3,4-trimethoxybenzyl)piperazine-4-yl)-2-hydroxy-1-propanesulfonic acid sodium salt (made according to Example 3) and 60 ml of dichloromethane are placed. Then 1.5 g (15 mmol) of triethylamine is added dropwise at room temperature, the mixture is cooled with ice. The solution of 1.23 g (10 mmol) of acetyl bromide in 20 ml of dichloromethane is added dropwise for 20 min, maintaining the reaction mixture temperature at 10÷15° C. Then the mixture is stirred for 1 h at 20° C. The mixture is evaporated to dryness in vacuum at 50÷60° C. The residue is treated with 100 ml of ethanol and refluxed with stirring for 0.5 h. The hot mixture is filtered off. The filtrate is concentrated in vacuum (~20 mm Hg) down to ¼ of the initial volume. The precipitate is filtered off, washed with (3×50 ml) of acetone. The white powder is dried for 12 h at 40° C.

Yield of $C_{19}H_{29}N_2O_8SNa*H_2O$, 2-acetoxy-3-(4-(2,3,4-trimethoxyphenyl)-methyl)piperazine-1-yl)propane-1-sulfonic acid sodium salt monohydrate—2.9 g (60%). Elemental analysis $C_{19}H_{29}N_2O_8SNa*H_2O$. Calc., %: C, 46.91; N, 6.42; N, 5.76. Found, %: C, 46.85; N, 6.40; N, 5.79. Mass spectrum, found: m/z 468.55. Calc.: M 468.50.

Example 16

The study of antiaggregant and anticoagulant properties of N,N'-substituted piperazines on the sample of donor human blood. The blood was collected by donor ulnar vein punction with dry sharp needle without syringe. The administration of drugs that influence on thrombocyte function was cancelled in 7÷10 days before the experiment.

In graduated plastic centrifuge tube 1 ml of 3.8% basic trisodium citrate solution with pH=7.4 was placed. The ulnar vein was punctuated, the freely effluent blood was collected up to 10 ml mark, the mixture was instantly stirred to prevent air bubbles appearance. The collected and stabilized blood was split in two 5 ml portions in two tubes.

To obtain thrombocyte enriched plasm the stabilized blood was spinned at 1000 rpm (150 g) for 8 min at room temperature. The repeated spinning of the blood at 3200 rpm (2300 g) for 20 min at 22° C. yielded thrombocyte depleted plasm.

The study of anticoagulant activity was done within 2 h after thrombocyte enriched plasm obtaining. The plasm was normalized to achieve thrombocyte concentration of 200-250×10$^9$/L by addition of thrombocyte-free plasm. The concentration of thrombocytes was measured on SOLAR AR 2110 analyzer.

Antiaggregant properties of N,N'-substituted piperazines were evaluated by their influence on thrombocyte aggregation in tests with ADP-, collagen- and ristocetin-induced aggregation. To dissolve N,N'-substituted piperazines and to dilute reagents Tris-HCl-buffer with pH=7.4 was used.

As the general characteristic of thrombocyte aggregation activity the maximum amplitude (MA) of aggregation was taken on. That is the peak value of transmittance coefficient of the sample after aggregation agent introduction expressed in % relative to the transmittance of thrombocyte-free plasm. The response was registered on ascending linear segment of aggregation curve for 16 s.

The measurements were done using 4-channel CHRONO-LOG 490-4D analyzer (CHRONO-LOG, USA). The temperature in the cell was 37° C., the spinning speed of magnetic stirrer was 1200 rpm.

In a cuvette 0.5 ml of N,N'-substituted piperazine solution was placed, then 0.4 ml of normalized thrombocyte plasm was added. The mixture was stirred and incubated at 37° C. for 5 min. The cuvette was placed in aggregometer, then 0.05 ml of aggregation inductor solution was added (ADP or collagen or ristocetin). Thrombocyte aggregation was measured for 3 min.

ADP-induced reversible thrombocyte aggregation test utilized CHRONO-PAR ADP reagent (CHRONO-LOG, USA) with 10 mol concentration. Primary (reversible) thrombocyte aggregation was evaluated by the response on addition of ADP threshold dose (ADP concentration is 1 mol) to plasm.

In collagen-induced thrombocyte aggregation test CHRONO-PAR COLLAGEN reagent (CHRONO-LOG, USA) was diluted with buffer solution until collagen concentration reached 10 g/ml.

To study ristocetin-induced thrombocyte aggregation CHRONO-PAR RISTOCETIN reagent (CHRONO-LOG, USA) was diluted with buffer solution until ristocetin concentration reached 12 mg/ml. Thrombocyte aggregation amplitude was measured in 60 s after the beginning of the reaction.

The study of antiaggregant properties of N,N'-substituted piperazines with arachidonic acid (CHRONO-LOG, USA) as an inductor: to 450 l of thrombocyte plasm 50 l of N,N'-substituted piperazine solution was added, the mixture was incubated in the cuvette of CHRONO-LOG aggregometer for 15 min at 36° C. The concentration of arachidonic acid in the sample was 0.2 mmol, the concentrations of N,N'-substituted piperazines and comparison substance (aspirin) were 4÷5 mmol/L.

It was shown that N,N'-substituted piperazines have pronounced aspirin-like activity by inhibiting thrombocyte aggregation induced by arachidonic acid (table 5).

To study anticoagulant properties of N,N'-substituted piperazines activated partial thromboplastin time (APTT) was measured. That is the ability of N,N'-substituted piperazines to increase thrombocyte depleted plasm coagulation time compared to the ability of control sample. The set of reagents for APTT determination (Russian Scientific Research Institute of Hematology and Transfusiology Ministry of Health of Russian Federation by Technical Regulation 9398-214-01966456-99) and COAG-A-MATE® XM coagulometer (ORGANON TEKNIKA, USA) were used.

The solutions of N,N'-substituted piperazines were mixed with thrombocyte depleted plasm at 1:1 ratio, then 0.1 ml of APTT reagent was added, the mixture was incubated in the cuvette for 5 min at 37° C., then 0.1 ml of 0.277% $CaCl_2$ solution was added. The time of coagulation (in seconds) was measured.

The results of the study of N,N'-substituted piperazines properties are shown in tables 1-5. As it appears from the data, N,N'-substituted piperazines are the compounds having selective influence on coagulation cascade factors, antiaggregant and anticoagulant activity. Antiaggregant and anticoagulant activity of the compounds of the invention exceeds the activity of the other drugs.

TABLE 1

Antiaggregant properties of N,N'-substituted piperazines and the reference drug Ozagrel.
ADP-induced thrombocyte aggregation.

| Aggregation parameters | Conc., mmol/L | | | | | | |
|---|---|---|---|---|---|---|---|
| | 0 (control) | 0.2 | 0.5 | 1.25 | 2.50 | 5.0 | 7.5 |
| Ozagrel (n = 10) | | | | | | | |
| MA, % (n = 10) | 13.2 ± 2.6 | — | — | 12.9 ± 2.1 | 10.6 ± 2.5 | 9.6 ± 2.5 | 4.2 ± 1.2 |
| $(MA_0-MA_x): MA_0 * 100\%$ | — | — | — | 2.3 | 19.7 | 63.6 | 68.2 |
| N,N'-substituted piperazine of example 8 | | | | | | | |
| MA, % (n = 10) | 19.0 ± 4.5 | 18.5 ± 2.8 | 14.3 ± 3.0 | 8.5 ± 2.8 | 2.5 ± 1.6 | — | — |
| $(MA_0-MA_x): MA_0 * 100\%$ | — | 2.6 | 24.7 | 55.3 | 86.8 | — | — |
| N,N'-substituted piperazine of example 5 | | | | | | | |
| MA, % (n = 10) | 15.3 ± 2.1 | 14.9 ± 2.0 | 11.5 ± 1.3 | 5.3 ± 2.2 | 1.9 ± 0.4 | — | — |
| $(MA_0-MA_x): MA_0 * 100\%$ | — | 2.7 | 24.8 | 65.4 | 87.8 | — | — |
| N,N'-substituted piperazine of example 1 | | | | | | | |
| MA, % (n = 5) | 13.7 ± 2.1 | 6.4 ± 1.1 | 5.0 ± 1.1 | 4.1 ± 0.7 | 3.0 ± 12.1 | 1.3 ± 0.5 | — |
| $(MA_0-MA_x): MA_0 * 100\%$ | — | 53.3 | 63.5 | 70.1 | 78.1 | 90.5 | — |
| N,N'-substituted piperazine of example 2 | | | | | | | |
| MA, % (n = 10) | 19.3 ± 2.0 | — | — | 15.0 ± 1.8 | 8.7 ± 2.2 | 3.1 ± 0.8 | — |
| $(MA_0-MA_x): MA_0 * 100\%$ | — | — | — | 21.1 | 55.0 | 84.2 | — |
| N,N'-substituted piperazine of example 4 | | | | | | | |
| MA, % (n = 5) | 18.3 ± 3.4 | — | — | 10.6 ± 2.0 | 5.7 ± 1.1 | 1.7 ± 0.5 | — |
| $(MA_0-MA_x): MA_0 * 100\%$ | — | — | — | 42.1 | 68.9 | 90.7 | — |
| N,N'-substituted piperazine of example 12 | | | | | | | |
| MA, % (n = 10) | 15.7 ± 2.0 | 14.1 ± 2.0 | 11.2 ± 3.3 | 5.1 ± 2.2 | 1.7 ± 0.3 | — | — |
| $(MA_0-MA_x): MA_0 * 100\%$ | — | 10.2 | 28.7 | 67.5 | 89.2 | — | — |
| N,N'-substituted piperazine of example 13 | | | | | | | |
| MA, % (n = 10) | 15.7 ± 2.0 | 14.0 ± 3.9 | 10.3 ± 1.3 | 4.7 ± 2.1 | 1.4 ± 0.2 | — | — |
| $(MA_0-MA_x): MA_0 * 100\%$ | — | 10.8 | 34.4 | 70.1 | 91.1 | — | — |

TABLE 2

Antiaggregant properties of N,N'-substituted piperazines. Collagen-induced thrombocyte aggregation.

| Aggregation parameters | Conc., mmol/L | | | | | | |
|---|---|---|---|---|---|---|---|
| | 0 (Control) | 0.2 | 0.5 | 1.25 | 2.5 | 5.0 | 7.5 |
| Ozagrel (therapeutical activity analog) | | | | | | | |
| MA, % (n = 10) | 76.7 ± 9.1 | — | 74.3 ± 7.9 | 64.1 ± 12.0 | 60.0 ± 2.5 | 54.0 ± 12.9 | 34.2 ± 11.2 |
| $(MA_0-MA_x): MA_0 * 100\%$ | — | — | 3.1 | 16.4 | 21.8 | 29.6 | 55.4 |

TABLE 2-continued

Antiaggregant properties of N,N'-substituted piperazines. Collagen-induced thrombocyte aggregation.

| Aggregation parameters | Conc., mmol/L | | | | | | |
|---|---|---|---|---|---|---|---|
| | 0 (Control) | 0.2 | 0.5 | 1.25 | 2.5 | 5.0 | 7.5 |
| N,N'-substituted piperazine of example 8 | | | | | | | |
| MA, % (n = 10) | 76.3 ± 7.5 | — | 72.3 ± 6.3 | 63.5 ± 9.8 | 58.5 ± 9.6 | 51.3 ± 7.9 | — |
| $(MA_0-MA_x):MA_0 * 100\%$ | — | — | 5.2 | 16.8 | 23.3 | 32.8 | — |
| N,N'-substituted piperazine of example 5 | | | | | | | |
| MA, % (n = 10) | 78.7 ± 4.8 | — | 74.5 ± 4.3 | 63.7 ± 2.2 | 23.9 ± 0.3 | — | — |
| $(MA_0-MA_x):MA_0 * 100\%$ | — | — | 5.3 | 19.1 | 69.8 | — | — |
| N,N'-substituted piperazine of example 1 | | | | | | | |
| MA, % (n = 5) | 74.0 ± 1.7 | — | 70.0 ± 5.1 | 60.7 ± 7.7 | 18.4 ± 3.1 | 2.1 ± 0.4 | — |
| $(MA_0-MA_x):MA_0 * 100\%$ | — | — | 5.4 | 18.8 | 75.1 | 97.2 | — |
| N,N'-substituted piperazine of example 2 | | | | | | | |
| MA, % (n = 10) | 79.3 ± 2.0 | — | 73.0 ± 7.3 | 65.10 ± 1.8 | 58.7 ± 2.9 | 24.1 ± 0.8 | — |
| $(MA_0-MA_x):MA_0 * 100\%$ | — | — | 7.9 | 17.9 | 26.0 | 69.6 | — |
| N,N'-substituted piperazine of example 4 | | | | | | | |
| MA, % (n = 5) | 75.7 ± 3.4 | — | — | 59.0 ± 5.9 | 52.2 ± 7.9 | 26.2 ± 3.5 | — |
| $(MA_0-MA_x):MA_0 * 100\%$ | — | — | — | 22.1 | 31.0 | 65.4 | — |
| N,N'-substituted piperazine of example 12 | | | | | | | |
| MA, % (n = 10) | 76.9 ± 7.1 | — | 71.9 ± 5.1 | 63.1 ± 9.1 | 55.4 ± 9.0 | 51.0 ± 7.1 | — |
| $(MA_0-MA_x):MA_0 * 100\%$ | — | — | 6.5 | 16.8 | 28.0 | 35.0 | — |
| N,N'-substituted piperazine of example 13 | | | | | | | |
| MA, % (n = 10) | 77.7 ± 5.5 | — | 72.1 ± 6.3 | 62.0 ± 9.8 | 55.0 ± 9.2 | 48.7 ± 7.1 | — |
| $(MA_0-MA_x):MA_0 * 100\%$ | — | — | 7.2 | 20.2 | 29.2 | 37.3 | — |

TABLE 3

Antiaggregant properties of N,N'-substituted piperazines. Ristocetin-induced thrombocyte aggregation.

| Aggregation parameters | Conc., mmol/L | | | | | |
|---|---|---|---|---|---|---|
| | 0 (Control) | 0.2 | 0.5 | 1.25 | 2.5 | 5.0 |
| Ozagrel (therapeutical activity analog) | | | | | | |
| MA (60 c), % (n = 10) | 63.7 ± 10.2 | — | — | 58.6 ± 9.1 | 45.6 ± 9.5 | 35.6 ± 8.5 |
| $(MA_0-MA_x):MA_0 * 100\%$ | — | — | — | 8.0 | 28.4 | 44.1 |
| N,N'-substituted piperazine of example 13 | | | | | | |
| MA (60 c), % (n = 10) | 62.2 ± 9.0 | 60.1 ± 8.1 | 48.2 ± 7.5 | 43.0 ± 4.8 | 35.2 ± 7.6 | 32.1 ± 5.5 |
| $(MA_x-MA_0):MA_0 * 100\%$ | — | 1.8 | 22.5 | 30.9 | 43.4 | 48.4 |
| N,N'-substituted piperazine of example 8 | | | | | | |
| MA (60 c), % (n = 10) | 60.4 ± 9.5 | 60.4 ± 9.1 | 50.7 ± 8.7 | 48.0 ± 5.8 | 39.2 ± 11.6 | 33.4 ± 9.9 |
| $(MA_x-MA_0):MA_0 * 100\%$ | — | — | 16.1 | 20.5 | 35.1 | 44.7 |

TABLE 3-continued

Antiaggregant properties of N,N'-substituted piperazines. Ristocetin-induced thrombocyte aggregation.

| Aggregation parameters | Conc., mmol/L | | | | | |
|---|---|---|---|---|---|---|
| | 0 (Control) | 0.2 | 0.5 | 1.25 | 2.5 | 5.0 |
| N,N'-substituted piperazine of example 3 | | | | | | |
| MA (60 c), % (n = 10) | 67.1 ± 8.9 | — | 63.0 ± 6.1 | 62.1 ± 8.9 | 51.0 ± 7.2 | 25.1 ± 3.2 |
| $(MA_x-MA_0): MA_0 * 100\%$ | — | — | 6.1 | 7.5 | 24.0 | 77.5 |
| N,N'-substituted piperazine of example 1 | | | | | | |
| MA (60c), % (n = 5) | 71.3 ± 2.1 | — | 70.0 ± 10.5 | 62.1 ± 7.7 | 55.1 ± 11.1 | 33.3 ± 4.5 |
| $(MA_x-MA_0): MA_0 * 100\%$ | — | — | 1.8 | 12.9 | 22.7 | 53.3 |

TABLE 4

Anticoagulant properties of N,N'-substituted piperazines.

| Coagulation parameters | Conc., mmol/L | | | | | | | |
|---|---|---|---|---|---|---|---|---|
| | 0 (Control) | 0.85 | 1.7 | 2.5 | 4.1 | 6.3 | 8.3 | 12.5 |
| Ozagrel (therapeutical activity analog) | | | | | | | | |
| APTT, sec (n = 5) $(APTT_x-APTT_0):APTT_0 * 100\%$ | 48.3 ± 4.0 | — | — | 51.8 ± 1.7 7.2 | 53.1 ± 3.0 10.0 | — | 57.9 ± 2.5 19.9 | 62.7 ± 2.1 29.8 |
| N,N'-substituted piperazine of example 3 | | | | | | | | |
| APTT, sec (n = 5) $(APTT_x-APTT_0):APTT_0 * 100\%$ | 53.7 ± 5.1 | — | 55.7 ± 3.2 3.4 | 58.3 ± 5.0 8.6 | 64.3 ± 3.7 19.7 | 73.4 ± 3.9 36.7 | 85.1 ± 3.2 58.5 | 110.1 ± 15.0 105.0 |
| N,N'-substituted piperazine of example 8 | | | | | | | | |
| APTT, sec (n = 5) $(APTT_x-APTT_0):APTT_0 * 100\%$ | 48.1 ± 4.6 | — | 61.1 ± 4.4 27.0 | 71.3 ± 5.2 56.5 | 91.1 ± 9.9 89.4 | — | 145.0 ± 7.3 201.5 | — |
| N,N'-substituted piperazine of example 5 | | | | | | | | |
| APTT, sec (n = 5) $(APTT_x-APTT_0):APTT_0 * 100\%$ | 56.4 ± 9.5 | — | 53.7 ± 7.0 -4.9 | 69.2 ± 5.9- 22.7 | 76.5 ± 9.8 35.6 | 98.9 ± 9.9 75.4 | >150 | — |
| N,N'-substituted piperazine of example 1 | | | | | | | | |
| APTT, sec (n = 5) $(APTT_x-APTT_0):APTT_0 * 100\%$ | 44.9 ± 7.3 | — | 50.4 ± 7.0 12.2 | 63.3 ± 5.7 40.1 | 70.4 ± 5.2 56.8 | — | 139.1 ± 9.5 209.8 | — |
| N,N'-substituted piperazine of example 12 | | | | | | | | |
| APTT, sec (n = 5) $(APTT_x-APTT_0):APTT_0 * 100\%$ | 45.8 ± 7.3 | — | 50.1 ± 4.0 9.4 | 63.2 ± 5.1 38.0 | 70.2 ± 3.2 53.3 | — | 140.0 ± 4.7 205.7 | — |

TABLE 5

Antiaggregant properties of N,N'-substituted piperazines and the reference drug Aspirin (standard thrombocyte aggregation inhibitor) induced by arachidonic acid. Thrombocyte aggregation induced by arachidonic acid.

| No | Compound | Conc., mmol/L | MA | Max. rate for 16 sec | % of aggregation inhibition |
|---|---|---|---|---|---|
| 1. | Buffer (control) | 0 | 87 | 139 | 0 |
| 2. | N,N'-substituted piperazine of example 5 | 4.0 | 2 | 1 | 100 |
| 3. | N,N'-substituted piperazine of example 7 | 4.5 | 72 | 49 | 35 |
| 4. | N,N'-substituted piperazine of example 1 | 4.5 | 33 | 20 | 60 |
| 5. | N,N'-substituted piperazine of example 13 | 4.0 | 2 | 1 | 100 |
| 6. | Acetylsalicylic acid (Aspirin, therapeutical activity analog) | 5 | 3 | 5 | 100 |

Example 17

The Investigation of Antiaggregant and Anticoagulant Properties of N,N'-Substituted Piperazines In Vivo

TABLE 6

Drug composition used for biological testing

| No | Component name | Amount, g |
|---|---|---|
| 1 | Composition 1 | |
| | N,N'- substituted piperazine as of Example 3 | 33 mmol or 8.3 mmol or 3.3 mmol or 1.7 mmol |
| | Sodium chloride | 9.0 |
| | Sodium hydroxide 0.1M solution | up to pH 7.2 |
| | Water | up to 1 L |
| 2 | Composition 2 | |
| | N,N'-substituted piperazine as of Example 1 | 3.3 mmol or 1.7 mmol |
| | Sodium chloride | 9.0 |
| | Sodium hydroxide 0.1M solution | up to pH 7.2 |
| | Water | up to 1 L |
| 3 | Composition 3 | |
| | N,N'- substituted piperazine as of Example 8 | 8.3 mmol or 3.3 mmol |
| | Sodium chloride | 9.0 |
| | Sodium hydroxide 0.1M solution | up to pH 7.2 |
| | Water | up to 1 L |
| 4 | Composition 4 | |
| | Ozagrel (activity analog) | 33 mmol or 8.3 mmol or 3.3 mmol |
| | Sodium chloride | 9.0 |
| | Sodium hydroxide 0.1M solution | up to pH 7.2 |
| | Water | up to 1 L |
| 5 | Composition 5 | |
| | N,N'- substituted piperazine as of Example 1 | 8.3 mmol or 3.3 mmol |
| | Sodium chloride | 9.0 |
| | Sodium hydroxide 0.1M solution | up to pH 7.2 |
| | Water | up to 1 L |
| 6 | Composition 6 | |
| | Ozagrel (activity analog) | 0.067 mmol (0.017 g) |
| | Lactose | 0.053 g |
| | Microcrystalline cellulose | 0.129 g |
| | Sodium stearylfumarate | 0.001 g |
| | TOTAL | 0.200 g |
| 7 | Composition 7 | |
| | N,N'- substituted piperazine as of Example 1 | 0.067 mmol (0.025 g) |
| | Lactose | 0.053 g |
| | Microcrystalline cellulose | 0.121 g |
| | Sodium stearylfumarate | 0.001 g |
| | TOTAL | 0.200 g |
| 8 | Composition 8 | |
| | N,N'- substituted piperazine as of Example 14 | 33 mmol or 8.3 mmol or 3.3 mmol |
| | Sodium chloride | 9.0 |
| | Sodium hydroxide 0.1M solution | up to pH 7.2 |
| | Water | up to 1 L |
| 9 | Composition 9 | |
| | N,N'-substituted piperazine as of Example 15 | 33 mmol or 8.3 mmol or 3.3 mmol |
| | Sodium chloride | 9.0 |
| | Sodium hydroxide 0.1M solution | up to pH 7.2 |
| | Water | up to 1 L |

The studies of N,N'-substituted piperazines in vivo were done on Wistar male rats with mass of 300±30 g (age of 15-25 weeks). The animals were kept with unlimited food and water allowance.

The influence of N,N'-substituted piperazines on ADP-induced thrombocyte aggregation parameters and blood fibrinolytic activity was studied.

Intravenous introduction (i/v): 1 ml of N,N'-substituted piperazine solution or 1 ml of comparison ozagrel solution were introduced via bolus injection into caudal vein of non-anaesthetized rats.

Oral introduction (orally): 0.2 g of the composition containing N,N'-substituted piperazine or comparison ozagrel sample (Table 6) were mixed with 1.5 ml of water, the suspension was orally introduced by means of rigid metal tube.

The dosing of active compound was calculated in mmol per 1 kg of rat's mass. Physiological solution (1.5 ml) was introduced in similar way as a control.

Immediately after the introduction the animals were put in separate standard cages for observation.

The collection of blood stabilized with heparin (50 units/ml) was done for 40÷60 s out of femoral vein under anaesthesia (thiopental sodium, 50 mg/kg intraperitoneally, in 1 ml of physiological solution). Blood to stabilizer ratio was 9:1. The blood was placed in siliconized tubes and stirred gently.

The study of thrombocyte aggregation activity was carried out using intact blood in 30 min after collection.

The measurements were done using AI-300 impedance aggregometer (Research and Manufacturing Association named after Comintern jointly with Almazov Cardiology Research Institute) at 37° C. and with constant stirring speed (1100 rpm) in intact medium (Ivanov V.I. etc. Inventor's Certificate SU 1504591 A1, 1989, issue N32). When sensor electrodes are in contact with stirred blood they are covered by thrombocyte monolayer. When inductor is introduced thrombocyte aggregation develops, as a result the amount of thrombocytes covering electrodes increases. Thickening of electrode covering layer due to thrombocyte aggregation leads to impedance increase between electrodes.

In the cuvette equipped with magnetic stirrer 0.55 ml of intact rat's blood was placed, then preliminary incubation was done for 2-3 min in thermostat at 37° C. Then the sensor was placed into the cuvette and the cuvette was moved into the special camera of the apparatus. After turning on the stirrer the aggregation inductor followed by disodium salt of ADP with concentration 0.25 mmol was added. Aggregation inductor volume to intact blood sample volume ratio was 1:12. The measurement of aggregation intensity was done by impedance method in 5 min after inductor introduction (Table 7).

TABLE 7

The influence of N,N'-substituted piperazines intravenous introduction on ADP-induced thrombocyte aggregation.

| | Control | Impedance, Ohm* | | | |
|---|---|---|---|---|---|
| Drug | (Phys. soln) | 0.1 mmol/kg | 0.025 mmol/kg | 0.01 mmol/kg | 0.005 mmol/kg |
| Composition 4 (Ozagrel), i/v | 5.0 ± 0.5 | 3.0 ± 0.6 | 3.5 ± 0.6 | 4.3 ± 0.2 | — |
| % of the control | — | 60 | 70 | 86 | |
| Composition 1, i/v | 5.8 ± 0.3 | 5.9 ± 0.3 | 5.5 ± 0.6 | 4.1 ± 0.4 | — |
| % of the control | — | 102 | 95 | 71 | |
| Composition 2, i/v | 5.8 ± 0.3 | — | — | 3.3 ± 0.4 | 4.4 ± 0.3 |
| % of the control | — | — | — | 57 | 76 |
| Composition 3, i/v | 5.0 ± 0.5 | — | 3.3 ± 0.8 | 3.9 ± 0.8 | — |
| % of the control | — | — | 66 | 78 | |
| Composition 6 (Ozagrel), orally | 5.7 ± 0.3 | 4.1 ± 0.2 | — | — | — |
| % of the control | — | 72 | — | — | — |
| Composition 7, orally | 5.7 ± 0.3 | 3.7 ± 0.2 | — | — | — |
| % of the control | — | 65 | — | — | — |

*$p < 0.05$ compared to control sample

The study of N,N'-substituted piperazines influence on rat's blood fibrinolytic activity was done by evaluation of spontaneous clots lysis time. The clots were obtained from euglobulin plasm fraction. This method is one among integral methods of fibrinolytic system state evaluation.

The collection of blood stabilized with sodium citrate (3.2%) was done for 60 s out of femoral vein under anaesthesia (thiopental sodium, 50 mg/kg intraperitoneally, in 1 ml of physiological solution).

The ratio of blood to stabilizer was equal to 9:1. The stabilized blood was spinned for 10 min at 1200 g. Thrombocyte depleted plasma was treated with the reagent for spontaneous euglobulin fibrinolysis produced by <<Technologia-standart>> LTD (Russia, Barnaul). Before measurement the reagents were diluted with distilled water to achieve the concentration of calcium chloride 0.277%, acetic acid 1%.

To obtain euglobulin plasm fraction 8 ml of water for injection, 0.18 ml of 1% acetic acid and 0.5 ml of plasm were mixed in consecutive order in the tube. The mixture was incubated at 4÷8° C. for 30 min, then spinned at 600 g for 5 min. Supernatant liquid was discharged, the tube was turned over and kept above the filter paper for 1 min. The residual euglobulin precipitate on the bottom of the tube was diluted with 0.5 ml of working buffer solution.

To the tube containing 0.5 ml of euglobulin solution 5 ml of 0.277% $CaCl_2$ solution were added, the mixture was stirred gently avoiding shaking, incubated on the water bath at 37° C. The time elapsed (in min) from the moment of $CaCl_2$ solution addition to complete dissolution of the clot was measured. Normally healthy rats have spontaneous euglobulin lysis time within 90-180 min range. The shortening of lysis time evidences of activation, the prolongation evidences of inhibition of fibrinolysis (Table 8).

TABLE 8

Fibrinolytic activity of N,N'-substituted piperazines.

| | Control | Spontaneous clot lysis time, min* | | |
|---|---|---|---|---|
| Drug | (Phys. soln) | 0.10 mmol/kg | 0.025 mmol/kg | 0.01 mmol/kg |
| Composition 4 (Ozagrel, activity analog), i/v | 129 ± 12 | — | 203 ± 31 | 173.8 ± 36.4 |
| % of the control | — | — | 157 | 134 |
| Composition 1, i/v | 129 ± 12 | — | 161 ± 21 | 176 ± 15 |
| % of the control | — | — | 125 | 136 |
| Composition 3, i/v | 129 ± 12 | — | 158 ± 8 | 223 ± 24 |
| % of the control | — | — | 122 | 172 |
| Composition 5, i/v | 129 ± 12 | — | 212 ± 8 | 230 ± 24 |
| % of the control | — | — | 164 | 178 |
| Composition 6 (Ozagrel), orally | 122 ± 10 | 190 ± 21 | — | — |
| % of the control | — | 156 | — | — |
| Composition 7, orally | 122 ± 10 | 199 ± 17 | — | — |
| % of the control | — | 163 | — | — |

*$p < 0.05$ compared to control sample

Example 18

The Study of N,N'-Substituted Piperazines Influence on Hemostasis System. Experimental Thrombosis Model The studies were done on Wistar male rats with mass of 230±30 g (laboratory animals nursery "Rappolovo", RAMS). The animals were kept with unlimited food (standard ration for laboratory rats K-120 by <<Inform-korm>>, Russia) and water allowance.

The drugs were introduced via bolus injection into caudal vein of non-anaesthetized rats. Physiological solution (5 ml/kg) was introduced in similar way as a control. Immediately after the introduction the animals were put in separate standard cages for observation.

Thrombosis modeling: the drugs were introduced into left femoral vein, in 50 min afterwards 1 ml of Bengal rose A photosensitizer (Acros Organics, USA) solution was introduced with dose of 17 mg/kg [Boselli 2007, Petrischev 2009].

Then the incision of internal surface of animal right thigh about 2 cm in length was made. The section of the femoral vein about 5 mm in length was released from surrounding tissues and separated from neurovascular bundle. Beneath this section of the vein the black non-transparent plastic strip 3 mm in width was laid to screen off the vein and surrounding tissues from radiation. The irradiation was done using diode laser <<DPSS-laser>> (Diode Pumped Solid State Laser, South Korea) with 532 nm wavelength and 60 mW power. The area of irradiation was 1 mm$^2$, exposing time was 40 min. The blood flow in femoral artery was measured by high frequency Doppler ultrasonography method (<<Minimax-Doppler-K>> apparatus, frequency of sensor was 20 MHz). The blood velocity alteration due to irradiation was measured (Table 9).

through inferomedian incision. To study microcirculation in mesentery venules and arterioles in transmitted light the rat was placed on thermostated microscope objective table. The application of noradrenalin solution (Aguettant, 2 mg/ml, Laboratoire AGUETTANT, France) was done directly on the mesentery (Furness J. B., Marshall J. M., 1974; Yantareva L. I., 2004).

The study of microcirculatory vessels was done with LUMAM I1 microscope (LOMO, Russia). The recording of video data was done with the camera (Optics and Electronics ISTA Ltd) attached to a personal computer. The processing of data was done with Video-Test 4.0 software (ISTA Ltd., Russia). The diameter of the vessel wall (D, m) before and after the application of noradrenalin and the starting time of blood flow slowdown induced by noradrenalin were measured (the measurements were done for 1 min after the application).

TABLE 9

The drug influence on alteration of arterial blood velocity in experimental photothrombosis.

| Drug; dose | V, cm/s* | | | | |
|---|---|---|---|---|---|
| | 0 min | 10 min | 20 min | 30 min | 40 min |
| N,N'- substituted piperazine as of Example 3; 0.01 mmol/kg | 7.1 ± 3.2 | 7.00 ± 2.4 | 7.5 ± 2.2 | 6.4 ± 1.9 | 6.6 ± 1.5 |
| N,N'- substituted piperazine as of Example 14; 0.01 mmol/kg | 6.9 ± 3.2 | 7.00 ± 2.0 | 6.8 ± 2.0 | 6.9 ± 1.3 | 6.6 ± 1.4 |
| Composition as of Example 6. Ozagrel (activity analog); 0.01 mmol/kg | 10.9 ± 2.9 | 5.7 ± 1.8 | Absence of blood flow | | |
| N,N'- substituted piperazine as of Example 3; 0.025 mmol/kg | 8.5 ± 1.7 | 8.4 ± 1.2 | 8.4 ± 3.0 | 8.9 ± 1.6 | 8.5 ± 1.2 |
| N,N'- substituted piperazine as of Example 14; 0.025 mmol/kg | 8.3 ± 1.8 | 8.1 ± 1.3 | 8.3 ± 2.0 | 8.0 ± 1.3 | 8.2 ± 1.2 |
| Composition as of Example 6. Ozagrel (activity analog); 0.025 mmol/kg | 9.0 ± 2.7 | 5.1 ± 1.7 | 3.8 ± 1.0 | 5.5 ± 1.4 | 5.8 ± 1.7 |

*$p < 0.05$ (n = 6)

Example 19

The Study of Vasodilator Properties of N,N'-Substituted Piperazines

Vasodilator properties of N,N'-substituted piperazines were evaluated according to their influence on microcirculatory vessel responsiveness.

The studies were done on Wistar male rats with mass of 300±30 g (laboratory animals nursery "Rappolovo", RAMS). The animals were kept with unlimited food (standard ration for laboratory rats K-120 by <<Inform-korm>>, Russia) and water allowance.

The solutions of N,N'-substituted piperazines and physiological (control) solution were introduced via bolus injection within 1 min into caudal vein of non-anaesthetized animals according to the dosage of 5.0 ml per 1 kg. Immediately after the introduction the animals were put in separate standard cages for observation.

In 30 min after the injection the animals were anaesthetized (thiopental sodium, 60 mg/kg intraperitoneally). The loop of small intestine adjoined to mesoappendix was retrieved

TABLE 10

Vasodilatory properties of N,N'-substituted piperazines.

| Drug; dose | $C_{NA}$* g/ml | Blood flow slowdown** | |
|---|---|---|---|
| | | % of vessel constriction | Latent period of slowdown, s |
| Venules | | | |
| Physiological solution (control) | $10^{-7}$ | 70 | 29 ± 4 |
| N,N'- substituted piperazine as of Example 14; 0.025 mmol/kg | $10^{-7}$ | 22 | No slowdown |
| Composition as of Example 6. Ozagrel (activity analog); 0.025 mmol/kg | $10^{-7}$ | 27 | No slowdown |
| Physiological solution (control) | $10^{-6}$ | 78 | 27 ± 6 |
| N,N'- substituted piperazine as of Example 14; 0.01 mmol/kg | $10^{-6}$ | 33 | 41 ± 6 |
| Composition as of Example 6. Ozagrel (activity analog); 0.01 mmol/kg | $10^{-6}$ | 44 | 32 ± 4 |

TABLE 10-continued

Vasodilatory properties of N,N'-substituted piperazines.

| Drug; dose | $C_{NA}$* g/ml | Blood flow slowdown** | |
|---|---|---|---|
| | | % of vessel constriction | Latent period of slowdown, s |
| Arterioles | | | |
| Physiological solution (control) | $10^{-7}$ | 80 | 34 ± 5 |
| N,N'- substituted piperazine as of Example 14; 0.025 mmol/kg | $10^{-7}$ | 28 | No slowdown |
| Composition as of Example 6. Ozagrel (activity analog); 0.025 mmol/kg | $10^{-7}$ | 27 | No slowdown |
| Physiological solution (control) | $10^{-6}$ | 85 | 20 ± 4 |
| N,N'- substituted piperazine as of Example 14; 0.01 mmol/kg | $10^{-6}$ | 58 | 43 ± 4 |
| Composition as of Example 6. Ozagrel (activity analog); 0.01 mmol/kg | $10^{-6}$ | 80 | 27 ± 6 |

*$C_{NA}$—concentration of noradrenalin.
**p < 0.05 compared to control sample (n = 6).

The carried out pharmaceutical and biological tests has shown that N,N'-substituted piperazines have antiaggregant, anticoagulant and vasodilator properties. The compositions based on N,N'-substituted piperazines have positive impact on haemostasis system recovery.

What is claimed is:

1. A compound of N,N'-substituted piperazine with a general formula (I):

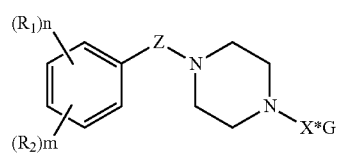

(I)

wherein $R_1$ and $R_2$ are selected from the group consisting of: linear or branched alkoxy ($C_1$-$C_4$), $CH_3C(=O)O$, and halogen; n=1-5; m=1-3; Z is selected from the group consisting of $CH_2$, C=O, and $SO_2$; X is selected from the group consisting of C(=NH)NH$_2$, C(=NH)NHC(=NH)NH$_2$, and $CH_2$(CHR$^3$)pCH$_2$SO$_3$H, where R$^3$ is selected from the group consisting of H, OH, $CH_3C(=O)O$, and OSO$_3$H; p=0-1; G is selected from the group consisting: of low molecular weight organic acid, or mineral acid, or sodium, or potassium, or ammonium cations, or water; and said compound possessing combined antiaggregant, antithrombotic, and vasodilator activity.

2. A compound of N,N'-substituted piperazine with a general formula (II):

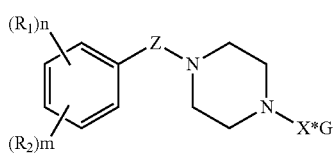

(II)

wherein $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$; X is selected from the group consisting of: C(=NH)NH$_2$, and C(=NH)NHC(=NH)NH$_2$, and G is low molecular weight organic acid, or mineral acid.

3. A method for synthesis of said compound according to claim 2, said method comprising the step of reacting N-substituted piperazine with a general formula:

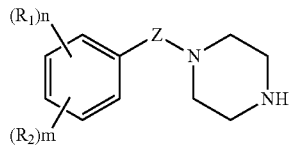

wherein $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$; with carboxamidating agents in organic solvents or in water at 10-50° C. in the presence of sodium carbonate.

4. A method for synthesis of said compound according to claim 2, said method comprising the steps of providing a hydrate of N-substituted piperazine with a general formula:

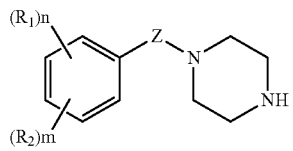

wherein $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$; and reacting said hydrate with carboxamidating agents in organic solvents or in water at 10-50° C. in the presence of bases.

5. A method for synthesis of said compound according to claim 2, said method comprising the steps of providing salts of N-substituted piperazine with a general formula:

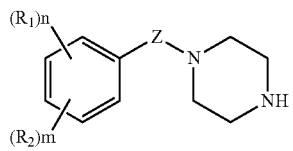

wherein $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$; and reacting said salts with carboxamidating agents in organic solvents or in water at 10-50° C. in the presence of bases.

6. The method for synthesis of N,N'-substituted piperazine of claim 3, wherein said carboxamidating agents are selected from the group consisting of: 1H-pyrazole-1-carboxamidine, dicyandiamide, salts of 1H-pyrazole-1-carboxamidine, and salts of dicyandiamide.

7. The method for synthesis of N,N'-substituted piperazine of claim 3, wherein said organic solvents are selected from the group consisting of: lower aliphatic alcohols, acetonitrile, tetrahydrofuran, dimethylformamide, dimethylsulfoxide, dichloromethane, and mixtures thereof.

8. A compound of N,N'-substituted piperazine with a general formula:

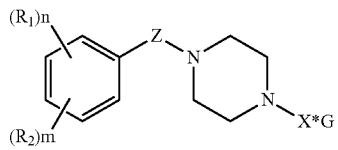

where $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$; X is $CH_2(CHR^3)pCH_2SO_3H$, where $R^3$ is selected from the group consisting of: H, OH, $CH_3C(=O)O$, and $OSO_3H$; p=0-1; and G is selected from the group consisting of: low molecular weight organic acid, mineral acid, sodium, potassium, ammonium cations, and water.

9. A method for synthesis of said compound of N,N'-substituted piperazine according to claim 8 comprising the step of reacting N-substituted piperazine with a general formula:

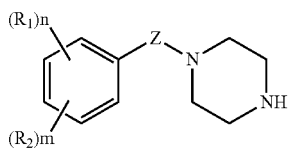

where $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$, with halogenalkylsulfonic acids or salts thereof in organic solvents, or in water at 10-100° C. in the presence of bases.

10. A method for synthesis of said compound according to claim 8, said method comprising the step of reacting a hydrate of N-substituted piperazine with a general formula:

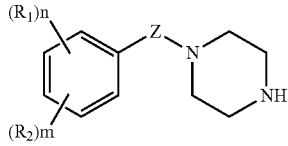

where $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$, with halogenalkylsulfonic acids or salts thereof in organic solvents, or in water at 10-100° C. in the presence of bases.

11. A method for synthesis of said compound according to claim 8, said method comprising the step of reacting salts of N-substituted piperazine with a general formula:

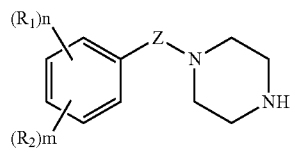

where $R_1$ and $R_2$ are selected from the group consisting of: linear or branched alkoxy ($C_1$-$C_4$), $CH_3C(=O)O$, and halogen; n=1-5; m=1-3; Z is selected from the group consisting of: $CH_2$, C=O, and $SO_2$, with halogenalkylsulfonic acids or salts thereof in organic solvents, or in water at 10-100° C. in the presence of bases.

12. The method for synthesis of said compound of N,N'-substituted piperazine according to claim 9, wherein said organic solvents are selected from the group consisting of: lower aliphatic alcohols, acetonitrile, tetrahydrofurane, dimethylformamide, dimethylsulfoxide, dichloromethane, chloroform, and mixtures thereof.

13. The method for synthesis of said compound of N,N'-substituted piperazine according to claim 9, wherein said halogenalkylsulfonic acids or salts thereof are selected from the group consisting of: 2-bromoethanesulfonic acid, 2-hydroxy-3-chloropropanesulfonic acid, and sodium salts thereof.

14. The method for synthesis of said compound of N,N'-substituted piperazine according to claim 9, wherein said bases are selected from the group consisting of: ammonia, sodium hydroxide, potassium hydroxide, sodium carbonate, sodium hydrogencarbonate potassium carbonate, and potassium hydrogencarbonate.

15. The compound according to claim 1, wherein said low molecular weight organic acid has a chain length $C_2$-$C_4$.

16. The compound according to claim 2, wherein said low molecular weight organic acid has a chain length $C_2$-$C_4$.

17. The compound according to claim 8, wherein said low molecular weight organic acid has a chain length $C_2$-$C_4$.

* * * * *